（12）United States Patent
Walt et al.

(10) Patent No.: US 8,932,869 B2
(45) Date of Patent: Jan. 13, 2015

(54) CHEMICAL SWITCHES FOR DETECTING REACTIVE CHEMICAL AGENTS

(75) Inventors: David R. Walt, Boston, MA (US); Sandra Bencic-Nagale, Lowell, MA (US)

(73) Assignee: Trustees of Tufts College, Boston, MA (US)

( * ) Notice: Subject to any disclaimer, the term of this patent is extended or adjusted under 35 U.S.C. 154(b) by 910 days.

(21) Appl. No.: 12/279,899

(22) PCT Filed: Feb. 22, 2007

(86) PCT No.: PCT/US2007/062568
§ 371 (c)(1),
(2), (4) Date: Jan. 15, 2010

(87) PCT Pub. No.: WO2008/048698
PCT Pub. Date: Apr. 24, 2008

(65) Prior Publication Data
US 2010/0227766 A1    Sep. 9, 2010

Related U.S. Application Data

(60) Provisional application No. 60/777,014, filed on Feb. 24, 2006.

(51) Int. Cl.
*G01N 21/64* (2006.01)
*C07D 311/82* (2006.01)
*G01N 33/00* (2006.01)
*C07D 219/06* (2006.01)

(52) U.S. Cl.
CPC .......... *G01N 33/0057* (2013.01); *G01N 21/643* (2013.01); *C07D 219/06* (2013.01)
USPC ............ 436/104; 436/103; 436/172; 549/388

(58) Field of Classification Search
None
See application file for complete search history.

(56) References Cited

U.S. PATENT DOCUMENTS

| 4,568,518 A | 2/1986 | Wolfbeis et al. |
| 4,767,206 A * | 8/1988 | Schwartz ..................... 356/73 |
| 4,784,699 A | 11/1988 | Cowsar et al. |
| 5,512,490 A | 4/1996 | Walt et al. |

(Continued)

FOREIGN PATENT DOCUMENTS

| CN | 1257891 A * | 6/2000 |
| WO | WO-02/28530 A2 * | 4/2002 |

OTHER PUBLICATIONS

English abstract and machine translation of Su et al., CN-1257891-A, Jun. 2000.*

(Continued)

*Primary Examiner* — Yelena G Gakh
*Assistant Examiner* — Michelle Adams
(74) *Attorney, Agent, or Firm* — Foley Hoag LLP

(57) ABSTRACT

Certain embodiments of the present invention relate to the preparation of microbeads that exhibit a "turn on" fluorescence response within seconds of exposure to an analyte vapor (e.g., a chemical warfare agent or a reactive stimulant). This sensing approach is modeled after the mechanism for inhibition of acetylcholinesterase enzyme activity, and utilizes a specific and irreversible reaction between phosphonyl halides and a fluorescent indicator. The present invention also relates to a sensor and a method for sensing an analyte through detection of changes in the fluorescing properties of the inventive microbeads.

20 Claims, 8 Drawing Sheets

(56) References Cited

U.S. PATENT DOCUMENTS

| | | | |
|---|---|---|---|
| 5,998,691 A | 12/1999 | Abel et al. | |
| 6,472,479 B1 * | 10/2002 | Kohler et al. | 525/344 |
| 7,348,181 B2 | 3/2008 | Walt et al. | |
| 2005/0090021 A1 | 4/2005 | Walt et al. | |
| 2005/0147534 A1 | 7/2005 | Swager et al. | |
| 2005/0153354 A1 | 7/2005 | Gilmanshin | |
| 2005/0196317 A1 | 9/2005 | Walt et al. | |
| 2005/0244952 A1 | 11/2005 | Cohen | |
| 2006/0029978 A1 | 2/2006 | O'Neill et al. | |

OTHER PUBLICATIONS

Albert, K. J., et al.; "High-Speed Fluorescence Detection of Explosives-like Vapors," *Analytical Chemistry*, 2000, 72, 1947-1955.

Albert, K. J., et al.; "Cross-Reactive Chemical Sensor Arrays," *Chemical Reviews* (Washington, D. C.) 2000, 100, 2595-2626.

Anitha, K., et al.; "Development of acetylcholinesterase silica sol-gel immobilized biosensor—an application towards oxydemeton methyl detection," *Biosensors & Bioelectronics* 2004, 20, 848-856.

Bencic-Nagale, S., et al.; "Extending the Longevity of Fluorescence-Based Sensor Arrays Using Adaptive Exposure," *Analytical Chemistry* 2005, 77, 6155-6162.

Dickinson, T. A., et al.; "A chemical-detecting system based on a cross-reactive optical sensor array," *Nature* (London) 1996, 382, 697-700.

Dickinson, T. A., et al.; "Convergent, Self-Encoded Bead Sensor Arrays in the Design of an Artificial Nose," *Analytical Chemistry* 1999, 71, 2192-2198.

Fan, C., et al.; "Electrochemical interrogation of conformational changes as a reagentless method for the sequence-specific detection of DNA," Proceedings of the National Academy of Sciences of the United States of America 2003, 100, 9134-9137.

Grate, J. W.; et al. "Selective Vapor Sorption by Polymers and Cavitands on Acoustic Wave Sensors: Is This Molecular Recognition?" Anal. Chem. 1996, 68, 913-7.

Hartmann-Thompson, C.; et al.; "Hydrogen-Bond Acidic Hyperbranched Polymers for Surface Acoustic Wave (SAW) Sensors," Chemistry of Materials 2004, 16, 5357-5364.

Jenkins, A. L., et al.; "Polymer-Based Lanthanide Luminescent Sensor for Detection of the Hydrolysis Product of the Nerve Agent Soman in Water," Analytical Chemistry 1999, 71, 373-378.

Jenkins, A. L., et al.; "Molecularly imprinted polymers for the detection of chemical agents in water," Polymeric Materials Science and Engineering 2001, 84, 76-77.

Kanan, S. M., et al.; "An Infrared Study of Adsorbed Organophosphonates on Silica: A Prefiltering Strategy for the Detection of Nerve Agents on Metal Oxide Sensors," Langmuir 2001, 17, 2213-2218.

Levitsky, I., et al.; "Rational Design of a Nile Red/Polymer Composite Film for Fluorescence Sensing of Organophosphonate Vapors Using Hydrogen Bond Acidic Polymers," Analytical Chemistry 2001, 73, 3441-3448.

Lin, Y., et al.; "Disposable Carbon Nanotube Modified Screen-Printed Biosensor for Amperometric Detection of Organophosphorus Pesticides and Nerve Agents," Electroanalysis 2004, 16, 145-149.

McGill, R. A.; et al. "Choosing polymer coatings for chemical sensors," Chemtech 1996, 24, 27-37.

Mortellaro, M. A., et al.; "A turn-on for optical sensing," Chemtech 1996, 26, 17-23.

Munkholm, C., et al.; "Polymer modification of fiber optic chemical sensors as a method of enhancing fluorescence signal for pH measurement," Analytical Chemistry 1986, 58, 1427-1430.

Pavlov, V., et al.; "Inhibition of the Acetycholine Esterase-Stimulated Growth of Au Nanoparticles: Nanotechnology-Based Sensing of Nerve Gases," *Nano Letters* 2005, 5, 649-653.

Ripoll, C., et al.; "Polyelectrolytes basiques faibles-II. Determination du $pK_a$ de la poly(vinyl-2 pyridine) et des coefficients d'activite des petits ions de la solution. Discussion et conclusion," *European Polymer Journal* 1971, 7, 1393-1409.

Ripoll, C., et al.; "Polyelectrolytes basiques faibles-II. Determination du $pK_a$ de la poly(vinyl-2 pyridine) et des coefficients d'activite des petits ions de la solution. Discussion et conclusion," *European Polymer Journal* 1971, 7, 1393-1409 [english abstract].

Simonian, A. L., et al.; "Enzyme-based biosensor for the direct detection of fluorine-containing organophosphates," Analytica Chimica Acta 2001, 442, 15-23.

Stitzel, S. E., et al.; "Array-to-Array Transfer of an Artificial Nose Classifier," Analytical Chemistry 2001, 73, 5266-5271.

Tomchenko, A., et al.; "Detection of chemical warfare agents using nanostructured metal oxide sensors," Sensors and Actuators B 2005, 108, 41-55.

Utriainen, M., et al.; "Combining miniaturized ion mobility spectrometer and metal oxide gas sensor for the fast detection of toxic chemical vapors," Sensors and Actuators, B: Chemical 2003, B93, 17-24.

Yang, Y., et al.; "Nerve Agents Detection Using a Cu2+/I-Cysteine Bilayer-Coated Microcantilever," Journal of the American Chemical Society 2003, 125, 1124-1125.

Yang, Y.-K., et al.; "A Rhodamine-Based Fluorescent and Colorimetric Chemodosimeter for the Rapid Detection of Hg2+ Ions in Aqueous Media," J. Am. Chem. Soc. 2005, 127, 16760-16761.

Yu, D., et al.; "Aqueous sol-gel encapsulation of genetically engineered *Moraxella* spp. cells for the detection of organophosphates," Biosensors & Bioelectronics 2005, 20, 1433-1437.

Zhang, S.-W., et al.; "Fluorescent Detection of Chemical Warfare Agents: Functional Group Specific Ratiometric Chemosensors," Journal of the American Chemical Society 2003, 125, 3420-3421.

Zhou, Y., et al.; "Potentiometric Sensing of Chemical Warfare Agents: Surface Imprinted Polymer Integrated with an Indium Tin Oxide Electrode," Analytical Chemistry 2004, 76, 2689-2693.

Zuyi, T., et al.; "Acidity and Alkali Metal Adsorption on the SiO2-Aqueous Solution Interface," Journal of Colloid and Interface Science 2002, 252, 15-20.

Munkholm, C. et al., "Intramolecular Fluorescence Self-Quenching of Fluoresceinamine", *J. Am. Chem. Soc.*, 112:2608-2612 (1990).

International Search Report dated Jun. 18, 2008.

* cited by examiner

NERVE AGENTS

Sarin

Soman

REACTIVE SIMULANT

DCP

NON-REACTIVE SIMULANTS

DIMP

DMMP i ii iii

[A]

[B]

| Sequence | A | B | C | D | E | F | G | H | I | J |
|---|---|---|---|---|---|---|---|---|---|---|
| ● | air | DMMP | toluene | ethanol | heptane | water | air | MS | DCP | air |
| △ | air | DMMP | DCP | air | DCP | heptane | toluene | air | water | air |
| ◇ | air | DMMP | DCP | toluene | water | heptane | MS | air | DCP | air |

Figure 8

| Vapor | v.p. (mm Hg at 25 °C) | Vapor concentration (ppm) | | |
|---|---|---|---|---|
| | | 50% | 25% | 10% |
| Diisopropyl methylphosphonate (DIMP) | 0.3 [a] | 200 | - | - |
| Dimethyl methylphosphonate (DMMP) | 1.6 [a] | 1000 | - | - |
| Diethyl chlorophosphate (DCP) | 0.10 [b] | 66 | 33 | 13 |
| Methyl salicylate (MS) | 1.0 [b,c] | 660 | - | - |
| Ethanol | 59 [d] | 39,000 | - | - |
| Heptane | 46 [d] | 30,000 | - | - |
| Toluene | 22 [d] | 14,000 | - | - |
| Water | 24 [d] | 16,000 | - | - |

US 8,932,869 B2

1

CHEMICAL SWITCHES FOR DETECTING REACTIVE CHEMICAL AGENTS

RELATED APPLICATIONS

This application claims the benefit of priority to Patent Cooperation Treaty Application number PCT/US2007/062568, filed Feb. 22, 2007; which claims the benefit of priority to U.S. Provisional Patent Application Ser. No. 60/777,014, filed Feb. 24, 2006.

GOVERNMENT SUPPORT

This invention was made with government support under grant F49620-01-1-0395 awarded by the U.S. Air Force, Air Force Office of Scientific Research. The government has certain rights in the invention.

BACKGROUND OF THE INVENTION

Chemical sensors are devices that detect the presence and/or level of a particular chemical species (an "analyte") in the air, water, or another medium. There exists high demand for chemical sensor devices able to detect low concentrations of analytes in liquid and/or gaseous phases. Specificity to particular analytes (i.e., the ability of a sensor to distinguish one species from another) is also generally desired.

The threat of chemical attack with aqueous or gas-phase organophosphates has been the motivation for extensive chemical sensor research in recent years. Many existing sensing methods (e.g., electrochemical, surface acoustic wave, colorimetric, fluorescence- and luminescence-based) target fast, portable, and inexpensive recognition. Sensors used to detect vapor phase nerve agent release in populated areas rely on specificity and subsecond response to ensure that the released vapor is accurately identified. For example, existing organophosphate vapor sensors are based on materials (e.g., fluorescent indicators, polymers, metal oxides, and gold nanoparticles) developed for fast recognition of a specific phosphonate or other functional groups. For example, see: Lin, Y.; Lu, F.; Wang, J. *Electroanalysis* 2004, 16, 145-149; Zhou, Y.; Yu, B.; Shiu, E.; Levon, K. *Analytical Chemistry* 2004, 76, 2689-2693; Yu, D.; Volponi, J.; Chhabra, S.; Brinker, C. J.; Mulchandani, A.; Singh, A. K. *Biosensors & Bioelectronics* 2005, 20, 1433-1437; Anitha, K.; Mohan, S. V.; Reddy, S. J. *Biosensors & Bioelectronics* 2004, 20, 848-856; Simonian, A. L.; Grimsley, J. K.; Flounders, A. W.; Schoeniger, J. S.; Cheng, T. C.; DeFrank, J. J.; Wild, J. R. *Analytica Chimica Acta* 2001, 442, 15-23; Yang, Y.; Ji, H.-F.; Thundat, T. *Journal of the American Chemical Society* 2003, 125, 1124-1125; Hartmann-Thompson, C.; Hu, J.; Kaganove, S, N.; Keinath, S. E.; Keeley, D. L.; Dvornic, P. R. *Chemistry of Materials* 2004, 16, 5357-5364; Pavlov, V.; Xiao, Y.; Willner, I. *Nano Letters* 2005, 5, 649-653; Zhang, S.-W.; Swager, T. M. *Journal of the American Chemical Society* 2003, 125, 3420-3421; Jenkins, A. L.; Uy, O. M.; Murray, G. M. *Analytical Chemistry* 1999, 71, 373-378; Jenkins, A. L.; Yin, R.; Jensen, J. L.; Durst, H. D. *Polymeric Materials Science and Engineering* 2001, 84, 76-77; Levitsky, I.; Krivoshlykov, S. G.; Grate, J. W. *Analytical Chemistry* 2001, 73, 3441-3448; Utriainen, M.; Karpanoja, E.; Paakkanen, H. *Sensors and Actuators, B: Chemical* 2003, B93, 17-24; and Tomchenko, A.; Harmer, G. P.; Marquis, B. *Chemical Sensors* 2004, 20, 34-35.

Materials research has thus far focused mostly on discovering chemical entities that enable chemical warfare agent recognition, with less effort spent on sensor miniaturization

2 and integration. As a consequence, the current sensors are not specifically designed to fit within existing multiplex vapor detection systems, such as sensor arrays, including electronic noses. Integration into such arrays is important, as array platforms contain several sensor types that can detect a wide spectrum of harmful vapors, and nerve agents represent only a small percentage among them. The ability to detect toxic chemical agents is facilitated by sensors that can identify these agents in a variety of contexts including backgrounds containing high concentrations of non-toxic chemicals.

An "electronic nose system" may be a fluorescence-based array containing thousands of individually optically addressable micron-scale vapor sensors. Dickinson, T. A.; Michael, K. L.; Kauer, J. S.; Walt, D. R. *Analytical Chemistry* 1999, 71, 2192-2198; and Dickinson, T. A.; White, J.; Kauer, J. S.; Walt, D. R. *Nature (London)* 1996, 382, 697-700. Each array may be prepared by loading 3-5 μm diameter microbead sensors into 4.5 μm diameter wells, etched into a fiber-optic bundle. This technology is advantageous for multiplexing and accommodating newly developed microsensors for a number of reasons: microbead batches are highly reproducible and inexpensive to fabricate, the sensor library may be expanded at any point in time, individually addressable multiple replicates of different microbead sensor types are accommodated on a highly dense array platform, and the arrays respond to vapors in sub-second times. Albert, K. J.; Walt, D. R. *Analytical Chemistry* 2000, 72, 1947-1955; and Stitzel, S. E.; Cowen, L. J.; Albert, K. J.; Walt, D. R. *Analytical Chemistry* 2001, 73, 5266-5271.

A "cross-reactive vapor sensing array", also referred to as an electronic nose or artificial nose system, is an array where each sensor type is cross-reactive and responds to many vapors. Albert, K. J.; Lewis, N. S.; Schauer, C. L.; Sotzing, G. A.; Stitzel, S. E.; Vaid, T. P.; Walt, D. R. *Chemical Reviews (Washington, D.C.)* 2000, 100, 2595-2626. Although cross-reactive sensors can respond reversibly hundreds of times, they often delay vapor identification because the data must be evaluated using pattern recognition—a time-consuming process. Bencic-Nagale, S.; Walt, D. R. *Analytical Chemistry* 2005, 77, 6155-6162. Moreover, difficult vapor discrimination tasks, such as differentiation between nerve agents and their less harmful simulants, may prolong the data processing time; challenging vapor queries often require the extraction of extensive amounts of information from the sensors. Vapor detection tasks necessitating immediate answers should not employ sensors that require lengthy data processing; for such tasks, specific probes are preferable to cross-reactive sensors. Although some specific probes that react with the target vapor irreversibly present a drawback as they may be used only a single time, their rapid response speed and specificity overshadow the disadvantage in having to replace the array after a vapor release has occurred. In such cases, the value of having a rapid responding probe for a rare event makes replacement acceptable as long as the chemistry is designed to provide zero false positive results.

Unfortunately, many previously developed sensors are not sufficiently specific because they detect both reactive and non-reactive simulants; therefore, novel sensors are needed. Recently developed probe compounds have partially overcome the lack of specificity common in many phosphonate warfare sensors, as they react only with phosphonyl halides. Zhang, S.-W.; Swager, T. M. *Journal of the American Chemical Society* 2003, 125, 3420-3421; Swager, T. M. et al. U.S. Patent Application 2005/0147534; incorporated by reference. Their probe compounds are designed to detect acetylcholinesterase inhibitor phosphonates when they convert into fluorescent esters upon reaction with phosphonyl halides. In addition to specificity, sensitivity, and fast response, these probes are advantageous due to their turn-on behavior upon binding the target analyte. Advantages of turn-on sensors have also been demonstrated with rhodamine derivatives that fluoresce upon selectively reacting with mercury (II) ions. Yang, Y.-K.; Yook, K.-J.; Tae, J. *J. Am. Chem. Soc.* 2005, 127, 16760-16761. Turn-on sensors are more reliable than turn-off sensors because they are less prone to false positives. Mortellaro, M. A.; Nocera, D. G. *Chemtech* 1996, 26, 17-23; and Fan, C.; Plaxco, K. W.; Heeger, A. J. *Proceedings of the National Academy of Sciences of the United States of America* 2003, 100, 9134-9137. False positives are rarely observed with turn-on sensors because, unlike turn-off sensors, high background intensity and photobleaching minimally affect their overall response.

SUMMARY OF THE INVENTION

Certain embodiments of the present invention relate to the preparation of microbeads that exhibit a "turn on" fluorescence response within seconds of exposure to an analyte vapor (e.g., a chemical warfare agent or a reactive stimulant). This sensing approach is modeled after the mechanism for inhibition of acetylcholinesterase enzyme activity, and utilizes a specific and irreversible reaction between phosphonyl halides and a fluorescent indicator. The present invention also relates to a sensor and a method for sensing an analyte through detection of changes in the fluorescing properties of the inventive microbeads.

For example, one aspect of the invention relates to nerve-agent-specific microbead probes (e.g., for Sarin and Soman; FIG. 1) which could be integrated into a microarray platform. Because nerve agents possess reactive groups that inhibit acetylcholinesterase by covalent modification of its active site, the preparation of nerve agent probes that specifically bind reactive molecules, including simulants such as DCP (FIG. 1), which is an acetylcholinesterase inhibitor with effects similar to the nerve agents, is desirable. In certain embodiments, the probes would be non-responsive to less harmful compounds that lack a reactive acyl or phosphonyl halide functionality (e.g., simulants dimethyl methylphosphonate (DMMP) and diisopropyl methylphosphonate (DIMP)).

In certain embodiments, the present invention relates to the fabrication of microbeads by adsorbing fluoresceinamine (FLA) onto carboxylate-functionalized polymer microbeads coated with poly(2-vinylpyridine) (PVP). When these microbeads are subjected to DCP vapor, the conversion of FLA into a phosphamide causes a rapid and intense increase in fluorescence. In addition, the PVP layer provides a high density of proton-accepting pyridine nitrogen sites that neutralize the HCl molecules formed during the reaction, thereby maintaining high product fluorescence, even after vapor exposure. Importantly, no significant response is observed when the microbeads are subjected to other nerve agent simulants (e.g., a mustard gas simulant) or volatile organics. The size, sensitivity, and sub-second response of the microbeads of the invention make them suitable for nerve agent vapor detection and inclusion into microbead sensor arrays.

BRIEF DESCRIPTION OF THE FIGURES

FIG. 8 depicts a table showing vapor pressure (v.p.) data and concentrations of the compounds used. The concentrations calculated in ppm correspond to saturated vapors mixed with air, and the content of the saturated vapor flow is expressed in %. Key: (a) obtained from Taranenko, N.; Alarie, J.-P.; Stokes, D. L.; Vo-Dinh, T. *Journal of Raman Spectroscopy* 1996, 27, 379-384; (b) retrieved from MSDS Database; (c) T=54° C. and; (d) obtained from Nelson, G. O. *Gas mixtures: preparation and control*; Lewis Publishers, Inc., 1992.

DETAILED DESCRIPTION OF THE INVENTION

Definitions

Figure 1:
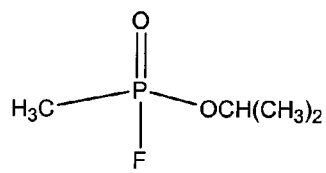
FIG. 1 depicts structures of various nerve agents and simulants thereof, and a reaction schematic of formation of FLPA (iii) upon reaction between the probe (i) and DCP (ii).
Figure 1:
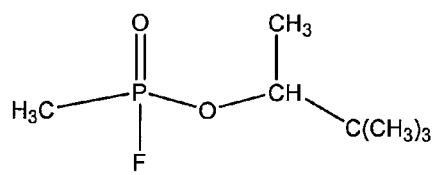
Figure 1:
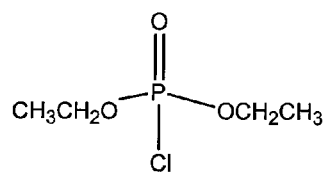
Figure 1:
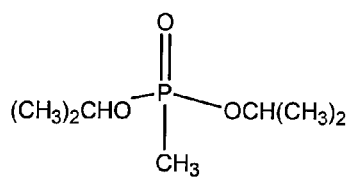
Figure 1:
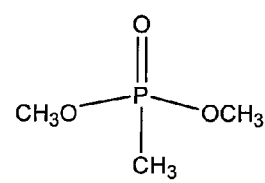
Figure 1:
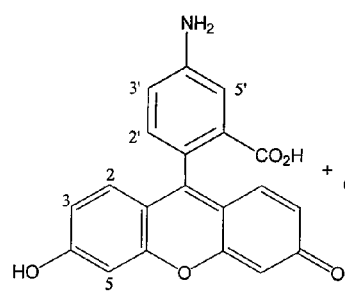
Figure 1:
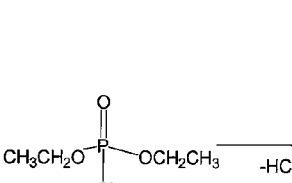
Figure 1:
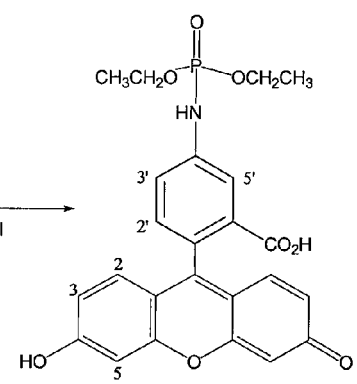

For convenience, definitions of certain terms employed in the specification, examples, and appended claims are collected here.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, "binding" can involve any hydrophobic, non-specific, or specific interaction.

The term "heteroatom" is art-recognized and refers to an atom of any element other than carbon or hydrogen. Illustrative heteroatoms include boron, nitrogen, oxygen, phosphorus, sulfur and selenium.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Unless the number of carbons is otherwise specified, "lower alkyl" refers to an alkyl group, as defined above, but having from one to about ten carbons, alternatively from one to about six carbon atoms in its backbone structure. Likewise, "lower alkenyl" and "lower alkynyl" have similar chain lengths.

The term "aralkyl" is art-recognized and refers to an alkyl group substituted with an aryl group (e.g., an aromatic or heteroaromatic group).

The terms "alkenyl" and "alkynyl" are art-recognized and refer to unsaturated aliphatic groups analogous in length and possible substitution to the alkyls described above, but that contain at least one double or triple bond respectively.

The term "aryl" is art-recognized and refers to 5-, 6- and 7-membered single-ring aromatic groups that may include from zero to four heteroatoms, for example, benzene, naphthalene, anthracene, pyrene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring may be substituted at one or more ring positions with such substituents as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, alkylthio, sulfonyl, sulfonamido, ketone, aldehyde, ester, heterocyclyl, aromatic or heteroaromatic moieties, trifluoroalkyl, cyano, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, aryls and/or heterocyclyls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "heterocyclyl", "heteroaryl", or "heterocyclic group" are art-recognized and refer to 3- to about 10-membered ring structures, alternatively 3- to about 7-membered rings, whose ring structures include one to four heteroatoms. Heterocycles may also be polycycles. Heterocyclyl groups include, for example, thiophene, thianthrene, furan, pyran, isobenzofuran, chromene, xanthene, phenoxanthene, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring may be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoroalkyl, cyano, or the like.

The terms "polycyclyl" or "polycyclic group" are art-recognized and refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle may be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, alkylthio, sulfonyl, ketone, aldehyde, ester, a heterocyclyl, an aromatic or heteroaromatic moiety, trifluoroalkyl, cyano, or the like.

The term "carbocycle" is art-recognized and refers to an aromatic or non-aromatic ring in which each atom of the ring is carbon.

The term "nitro" is art-recognized and refers to —$NO_2$; the term "halogen" is art-recognized and refers to —F, —Cl, —Br or —I; the term "sulfhydryl" is art-recognized and refers to —SH; the term "hydroxyl" means —OH; and the term "sulfonyl" is art-recognized and refers to —$SO_2^-$. "Halide" designates the corresponding anion of the halogens, and "pseudohalide" has the definition set forth on page 560 of "Advanced Inorganic Chemistry" by Cotton and Wilkinson, that is, for example, monovalent anionic groups sufficiently electronegative to exhibit a positive Hammett sigma value at least equaling that of a halide (e.g., CN, OCN, SCN, SeCN, TeCN, $N_3$, and $C(CN)_3$).

The terms "amine" and "amino" are art-recognized and refer to both unsubstituted and substituted amines, e.g., a moiety that may be represented by the general formulas:

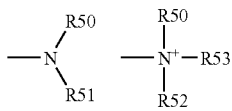

wherein R50, R51, R52 and R53 each independently represent a hydrogen, an alkyl, an alkenyl, —$(CH_2)_m$—R61, or R50 and R51 or R52, taken together with the N atom to which they are attached complete a heterocycle having from 4 to 8 atoms in the ring structure; R61 represents an aryl, a cycloalkyl, a cycloalkenyl, a heterocycle or a polycycle; and m is zero or an integer in the range of 1 to 8. In other embodiments, R50 and R51 (and optionally R52) each independently represent a hydrogen, an alkyl, an alkenyl, or —$(CH_2)_m$—R61. Thus, the term "alkylamine" includes an amine group, as defined above, having a substituted or unsubstituted alkyl attached thereto, i.e., at least one of R50 and R51 is an alkyl group.

The term "acylamino" is art-recognized and refers to a moiety that may be represented by the general formula:

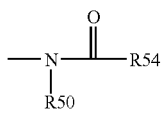

wherein R50 is as defined above, and R54 represents a hydrogen, an alkyl, an alkenyl or —$(CH_2)_m$—R61, where m and R61 are as defined above.

The term "amido" is art recognized as an amino-substituted carbonyl and includes a moiety that may be represented by the general formula:

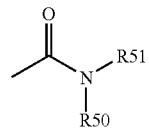

wherein R50 and R51 are as defined above. Certain embodiments of the amide in the present invention will not include imides which may be unstable.

The term "alkylthio" refers to an alkyl group, as defined above, having a sulfur radical attached thereto. In certain embodiments, the "alkylthio" moiety is represented by one of —S-alkyl, —S-alkenyl, —S-alkynyl, and —S—$(CH_2)_m$—R61, wherein m and R61 are defined above. Representative alkylthio groups include methylthio, ethyl thio, and the like.

The term "carboxyl" is art recognized and includes such moieties as may be represented by the general formulas:

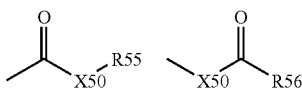

wherein X50 is a bond or represents an oxygen or a sulfur, and R55 and R56 represents a hydrogen, an alkyl, an alkenyl, —$(CH_2)_m$—R61 or a pharmaceutically acceptable salt, R56 represents a hydrogen, an alkyl, an alkenyl or —$(CH_2)_m$—R61, where m and R61 are defined above. Where X50 is an oxygen and R55 or R56 is not hydrogen, the formula represents an "ester". Where X50 is an oxygen, and R55 is as defined above, the moiety is referred to herein as a carboxyl group, and particularly when R55 is a hydrogen, the formula represents a "carboxylic acid". Where X50 is an oxygen, and R56 is hydrogen, the formula represents a "formate". In general, where the oxygen atom of the above formula is replaced by sulfur, the formula represents a "thiolcarbonyl" group. Where X50 is a sulfur and R55 or R56 is not hydrogen, the formula represents a "thiolester." Where X50 is a sulfur and R55 is hydrogen, the formula represents a "thiolcarboxylic acid." Where X50 is a sulfur and R56 is hydrogen, the formula represents a "thiolformate." On the other hand, where X50 is a bond, and R55 is not hydrogen, the above formula represents a "ketone" group. Where X50 is a bond, and R55 is hydrogen, the above formula represents an "aldehyde" group.

The term "carbamoyl" refers to —O(C═O)NRR', where R and R' are independently H, aliphatic groups, aryl groups or heteroaryl groups.

The term "oxo" refers to a carbonyl oxygen (═O).

The terms "oxime" and "oxime ether" are art-recognized and refer to moieties that may be represented by the general formula:

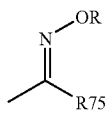

wherein R75 is hydrogen, alkyl, cycloalkyl, alkenyl, alkynyl, aryl, aralkyl, or —(CH$_2$)$_m$—R61. The moiety is an "oxime" when R is H; and it is an "oxime ether" when R is alkyl, cycloalkyl, alkenyl, alkynyl, aryl, aralkyl, or —(CH$_2$)$_m$—R61.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—R61, where m and R61 are described above.

The term "sulfonate" is art recognized and refers to a moiety that may be represented by the general formula:

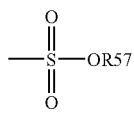

in which R57 is an electron pair, hydrogen, alkyl, cycloalkyl, or aryl.

The term "sulfate" is art recognized and includes a moiety that may be represented by the general formula:

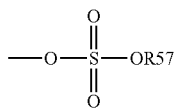

in which R57 is as defined above.

The term "sulfonamido" is art recognized and includes a moiety that may be represented by the general formula:

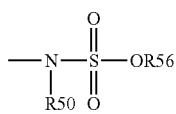

in which R50 and R56 are as defined above.

The term "sulfamoyl" is art-recognized and refers to a moiety that may be represented by the general formula:

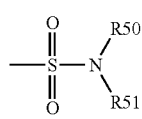

in which R50 and R51 are as defined above.

The term "sulfonyl" is art-recognized and refers to a moiety that may be represented by the general formula:

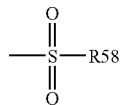

in which R58 is one of the following: hydrogen, alkyl, alkenyl, alkynyl, cycloalkyl, heterocyclyl, aryl or heteroaryl.

The term "sulfoxido" is art-recognized and refers to a moiety that may be represented by the general formula:

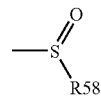

in which R58 is defined above.

The term "phosphoryl" is art-recognized and may in general be represented by the formula:

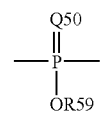

wherein Q50 represents S or O, and R59 represents hydrogen, a lower alkyl or an aryl. When used to substitute, e.g., an alkyl, the phosphoryl group of the phosphorylalkyl may be represented by the general formulas:

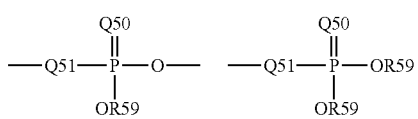

wherein Q50 and R59, each independently, are defined above, and Q51 represents O, S or N. When Q50 is S, the phosphoryl moiety is a "phosphorothioate".

The term "phosphoramidite" is art-recognized and may be represented in the general formulas:

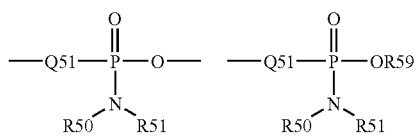

wherein Q51, R50, R51 and R59 are as defined above.

The term "phosphonamidite" is art-recognized and may be represented in the general formulas:

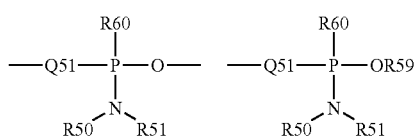

wherein Q51, R50, R51 and R59 are as defined above, and R60 represents a lower alkyl or an aryl.

Analogous substitutions may be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "selenoalkyl" is art-recognized and refers to an alkyl group having a substituted seleno group attached thereto. Exemplary "selenoethers" which may be substituted on the alkyl are selected from one of —Se-alkyl, —Se-alkenyl, —Se-alkynyl, and —Se—$(CH_2)_m$—R61, m and R61 being defined above.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The definition of each expression, e.g., alkyl, m, n, and the like, when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations.

As used herein, diisopropyl methylphosphonate is abbreviated as "DIMP"; dimethyl methylphosphonate is abbreviated as "DMMP"; diethyl chlorophosphate is abbreviated as "DCP"; methyl salicylate is abbreviated as "MS"; and acryloyl chloride is abbreviated "AC".

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, or other reaction.

The term "substituted" is also contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents may be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, "Handbook of Chemistry and Physics", 67th Ed., 1986-87, inside cover.

While several embodiments of the present invention are described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

Analytes

In one aspect, the invention provides a sensor that is capable of detecting electrophiles, i.e., analytes having electrophilic moieties, such as certain chemical warfare agents and/or insecticides. In some cases, the electrophile can be detected while in a gaseous or a liquid phase. Examples of chemical warfare agents that can be detected according to the invention include, but are not limited to, tabun (GA), sarin (GB), soman (GD), and cyclosarin (GF), phosgene, O-ethyl S-(2-diisopropylaminoethyl)methylphosphonothioate (VX), and thionyl chloride. The formula for tabun is $(CH_3)_2NP$(=O)(—CN)(—$OC_2H_5$); sarin is $CH_3$—P(=O)(—F)(—OCH$(CH_3)_2$); soman is $CH_3$P(=O)(—F)(—CH$(CH_3)$C$(CH_3)_3$); cyclosarin is $CH_3$—P(=O)(—F)(cyclohexane); VX is $CH_3$P(=O)(—$SCH_2CH_2$N[CH$(CH_3)_2]_2$)(—$OC_2H_5$). The same type of phosphorus compounds are used as, for example, insecticides. In the structure of insecticides P(=O) has generally been replaced by P(=S) and a less reactive group than (—F), (—CN) or (—$SCH_2CH_2$N[CH$(CH_3)_2]_2$) is used.

In one set of embodiments, the sensor is capable of detecting an electrophile that includes an electrophilic atom, such as an electrophilic phosphorous, sulfur, or arsenic atom (for example, a phosphate ester). In some cases, the electrophilic phosphorous, sulfur, or arsenic atom has more than one electronegative (i.e., electron-withdrawing) substituent on it. Examples of electronegative substituents include, but are not limited to, halogens, pseudohalogens, alkoxides, phenols, alkyls, alkenyls, alkynyls, or the like. For example, in some cases, the sensor may be capable of detecting an electrophile having structure A or B (as shown below):

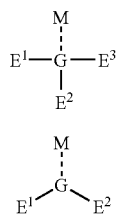

where $E^1$ is selected from electron-withdrawing moieties such as halogens, pseudohalogens, or alkoxide groups; $E^2$ and $E^3$ (when present) are either electron-withdrawing moieties, or are selected from the group consisting of hydrogen, alkyl, cycloalkyl, heterocycloalkyl, alkenyl, alkynyl, aryl, heteroaryl, aralkyl, and heteroaralkyl; G is an electrophilic phosphorous, sulfur, or arsenic atom; and M comprises an atom able to form a multiple bond (indicated by - - - ) with G, for example, nitrogen (e.g., an amine) or a chalcogen. In some cases, M may be an electron-withdrawing moiety. As an example, if M is oxygen, the electrophile may include a phosphate ester or an arsenic ester moiety. As used herein, "electrophilic" is given its ordinary definition as used in the art, e.g., a compound or moiety able to accept an electron pair from a molecule with which it forms a temporary or permanent covalent bond. Non-limiting examples of electrophiles having an electrophilic phosphorous, include compounds of structure C:

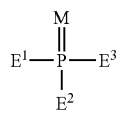

wherein M is O, S, or $NR^A$; $R^A$ is hydrogen, alkyl, acyl, or aralkyl; $E^1$ is F, Cl, Br or I; $E^2$ is hydroxyl, alkoxy, aryloxy, aralkoxy, acyloxy, thio, sulfonyl, sulfhydryl, sulfamoyl, sulfonamido, sulfate, sulfonate, sulfoxido, amino, imino, amido, trifluoroalkyl, cyano, $-O(CH_2)_m R^B$, $-NH(CH_2)_m R^B$, $-S(CH_2)_m R^B$; $E^3$ is hydrogen, alkyl, cycloalkyl, heterocycloalkyl, alkenyl, alkynyl, aryl, heteroaryl, aralkyl, heteroaralkyl, hydroxyl, alkoxy, aryloxy, aralkoxy, acyloxy, thio, sulfonyl, sulfhydryl, sulfamoyl, sulfonamido, sulfate, sulfonate, sulfoxido, amino, imino, amido, trifluoroalkyl, or cyano; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano (for instance, methyl, ethyl, propyl, isopropyl, butyl, isobutyl, pentyl, isopentyl, 1,2,2-trimethylpropyl, cyclopentyl, cyclohexyl, cycloheptyl, cyclohexenyl, phenyl or paranitrophenyl); and m is 0-10 inclusive.

In another set of embodiments, the sensor is capable of detecting an electrophile that includes an electrophilic carbon atom multiply-bonded to another electrophilic atom. For example, in some cases, the sensor may be capable of detecting an electrophile having structure D:

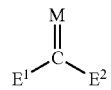

where $E^1$ and $E^2$ are electron withdrawing moieties such as halogens, pseudohalogens, or alkoxide groups, and M comprises an atom able to form a double bond with the carbon atom, for example, nitrogen (e.g., and amine) or a chalcogen, such as oxygen or sulfur. Non-limiting examples of such electrophiles include compounds having any of the following structures (E to H):

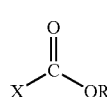

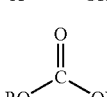

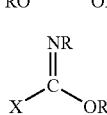

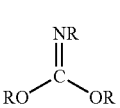

where X is halogen or pseudohalogen; and R is alkyl, aryl, or aralkyl, any of which may comprise one or more fluorine atoms.

As used herein, terms such as "electron-withdrawing" and "electron-poor" are given their ordinary meaning as used in the art, i.e., moieties generally deficient in electrons. Non-limiting examples of electron-withdrawing or electron-poor moieties include the halogens, amines, $-NH_3$, $-NO_2$, $-CN$, $-SCN$, $-OCN$, pyridinium, etc. Similarly, as used herein, terms such as "electron-donating" and "electron-rich" are also given their ordinary meaning as used in the art, i.e., moieties generally having an excess of electrons. Non-limiting examples of electron-rich or electron-donating moieties include $-OH$, $-OR$, $-NR_2$, $-NH_2$, thienyl, etc.

In some embodiments of the invention, the sensor is capable of detecting an electrophilic analyte that is or is able to be transformed to an acylating agent. As used herein, an "acylating agent" is given its ordinary definition as used in the art, i.e., an agent that has an acyl group able to react with a compound such that the acyl group is transferred to the compound and the compound forms a covalent bond with the acyl group (i.e., the compound becomes "acylated").

Microspheres

By "microspheres" (or "beads" or "particles" or grammatical equivalents herein) is meant small discrete particles. In certain embodiments, the microspheres of the invention have a diameter of between about 0.01 μm and about 1,000 μm. In certain embodiments, the microspheres of the invention have a diameter of between about 0.1 μm and about 100 μm. In certain embodiments, the microspheres of the invention have a diameter of between about 1 µm and about 10 µm. In certain embodiments, the microspheres of the invention have a diameter of between about 1 µm and about 5 µm. In certain embodiments, the microspheres of the invention have a diameter of about 3 µm.

The composition of the beads will vary, depending on the class of bioactive agent and the method of synthesis. Suitable bead compositions include those used in peptide, nucleic acid and organic moiety synthesis, including, but not limited to, plastics, ceramics, glass, polystyrene, methylstyrene, acrylic polymers, paramagnetic materials, thoria sol, carbon graphite, titanium dioxide, latex or cross-linked dextrans such as Sepharose, cellulose, nylon, cross-linked micelles and Teflon.

Synthetic beads may be fabricated by polymerizing or copolymerizing a variety of condensation or vinyl precursor monomers or by way of combinatorial polymer synthesis. Such polymers can be further modified by the addition of plasticizers, such as tritolyl phosphate (TTP), triphenyl phosphate (TTP) or dibutyl phthalate (DBP). Particularly useful dye-encoding bead candidates for use in sensor array subpopulations are polymer and copolymer materials which exhibit either a characteristic swelling upon exposure to various vapor analytes, a characteristic polarity difference due to their chemical structure, or a characteristic chemical adsorption response with various vapor analytes. In prescreening candidate polymers as bead materials and evaluating candidates based on desirable swelling, polarity and adsorption characteristics, two particularly useful references are: R. A. McGill, et al. *Chemtech* 1996, 24, 27-37; and J. W. Grate, et al. *Anal. Chem.* 1996, 68, 913-7.

A variety of bead chemistries may be utilized in fabricating a wide diversity of sensor bead subpopulations. For example, the following compositions have been found to be particularly useful as candidate bead materials: silica, poly(ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80-85%) dimethyl-(15-20%) (acryloxypropyl)methylsiloxane copolymer], PS901.5 [poly(acryloxypropyl-methyl)siloxane], PS851 [(97-98%) dimethyl-(2-3%) (methacryloxypropyl)methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, acrylic polymers, and poly(methyl styrene/divinyl benzene). In addition, other adsorbents, such as commercially available silica beads adapted with a variety of bonded phases for use in Phenomenex columns, such as beads comprising C8, C18 and phenyl hexyl, are useful as sensor bead matrices. Inorganic materials such as alumina and zeolites may also be utilized. Other polymers and copolymers having distinguishable and suitable swelling behavior, polarity and chemical adsorption characteristics are also anticipated as likely bead candidate materials. Particularly useful bead candidate materials include the polymers, copolymers, and polymerized monomers listed in Table 7, Table 8 and Table 10 of U.S. Pat. No. 5,512,490 to Walt, et al, which are herein incorporated by reference in their entirety.

In alternative embodiments, any synthesized or commercially available bead materials may be further modified by applying either a surface treatment or coating to modify the characteristic optical response signature. For example, where porous silica beads are utilized, N-octadecyltriethoxysilane or 3-(trimethoxysilyl)propyl methacrylate may be applied as a silanization treatment. In general, "Microsphere Detection Guide" from Bangs Laboratories, Fishers Ind. is a helpful guide.

In certain embodiments the microspheres of the invention comprise a reporting dye that, in combination with the characteristic bead matrix material, provides an optical response signature that can be used to identify the bead, and thus the attached analyte, as described in U.S. Pat. No. 5,512,490, and US Pat. App. No. 2005/0090021, both to Walt, et al., both incorporated by reference in their entirety. The reporter dye may be either a chromophore-type or a fluorophore-type, a fluorescent dye is preferred because the strength of the fluorescent signal provides a better signal-to-noise ratio when decoding.

In certain embodiment, polarity-sensitive dyes or solvatochromic dyes are utilized. Solvatochromic dyes are dyes whose absorption or emission spectra are sensitive to and altered by the polarity of their surrounding environment. Typically, these dyes exhibit a shift in peak emission wavelength due to a change in local polarity. Polarity changes which cause such wavelength shifts can be introduced by the bead matrix used for a particular sensor bead subpopulation or, the presence of a target analyte. The change in polarity creates a characteristic optical response signature which is useful for both encoding subpopulations of bead types and for detecting specific target analytes. For example, Nile Red is soluble in a wide range of solvents, is photochemically stable, and has a relatively strong fluorescence peak. Additional dyes which are conventionally known in the art and may be used as dyes in the present invention are those found in U.S. Pat. No. 5,512,490 to Walt, et al., see, e.g., Table 3, Table 4, Table 5, Table 6 and Table 11; incorporated herein by reference in their entirety.

Features such as bead material polarity, chemical structure, chemical functionality, bead surface area, bead pore size, bead swelling characteristics, or chemical adsorption behavior, either separately or in combination, contribute to the characteristic optical response signature of a given bead subpopulation. In one embodiment, bead materials which are permeable or semi-permeable to fluids including vapors and liquid analytes are preferred. In another embodiment, bead materials that swell upon contact with fluids such as vapor or liquid analytes are preferred. In general, bead materials which have unique polarity, structure, pore size, surface area, functionality or adsorption characteristics are particularly useful for sensor bead matrices of the present invention.

Microbead Sensors and Sensor Arrays

In certain embodiments, individual sensors are fabricated using a fluorescent indicator (solvatochromic, vapochromic, pH-sensitive, etc.) in combination with micrometer-sized silica or polymer beads, or polymer-coated silica microbeads (as described above). The polymers and surface groups can act as concentrators and/or adsorbents of organic vapors which help maximize interactions. Sensor responses reflect changes in fluorescence intensity and wavelength shifts that occur as vapors are presented to the sensor array. Many parameters (e.g., vapor diffusion through the polymer layer, polymer type, surface-vapor interactions, pulse time, and pulse regime) contribute to the optical response resulting in unique chemical signatures for a particular vapor-sensor combination. Each sensor stock contains millions of individual microbead sensors, allowing fabrication of thousands of arrays with highly reproducible sensor responses.

In certain embodiments, the present invention provides array compositions comprising the inventive microbeads. By "array" herein is meant a plurality of microbeads in an array format; the size of the array will depend on the composition and end use of the array. Arrays containing from about two different beads to many millions can be made, with very large fiber optic arrays being possible. Generally, the array will comprise from two to as many as a billion or more, depending on the size of the beads and the substrate, as well as the end use of the array, thus very high density, high density, moderate density, low density and very low density arrays may be made. Preferred ranges for very high density arrays are from about 10,000,000 to about 2,000,000,000, with from about 100,000,000 to about 1,000,000,000 being preferred. High density arrays range about 100,000 to about 10,000,000, with from about 1,000,000 to about 5,000,000 being particularly preferred. Moderate density arrays range from about 10,000 to about 50,000 being particularly preferred, and from about 20,000 to about 30,000 being especially preferred. Low density arrays are generally less than 10,000, with from about 1,000 to about 5,000 being preferred. Very low density arrays are less than 1,000, with from about 10 to about 1000 being preferred, and from about 100 to about 500 being particularly preferred. In some embodiments, the compositions of the invention may not be in array format; that is, for some embodiments, compositions comprising a single bioactive agent may be made as well. In addition, in some arrays, multiple substrates may be used, either of different or identical compositions. Thus for example, large arrays may comprise a plurality of smaller substrates.

In addition, one advantage of the present compositions is that particularly through the use of fiber optic technology, extremely high density arrays can be made. Thus for example, because beads of 200 nm can be used, and very small fibers are known, it is possible to have as many as 250,000 different fibers and beads in a 1 mm$^2$ fiber optic bundle, with densities of greater than 15,000,000 individual beads and fibers per 0.5 cm$^2$ obtainable.

The compositions comprise a substrate. By "substrate" or "solid support" or other grammatical equivalents herein is meant any material that can be modified to contain discrete individual sites appropriate for the attachment or association of beads and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, Teflon®, etc.), polysaccharides, nylon or nitrocellulose, resins, silica or silica-based materials including silicon and modified silicon, carbon, metals, inorganic glasses, plastics, optical fiber bundles, and a variety of other polymers. In general, the substrates should allow optical detection and not appreciably fluoresce.

Generally the substrate is flat or planar, although as will be appreciated by those in the art, other configurations of substrates may be used as well; for example, three dimensional configurations can be used, for example by embedding the beads in a porous block of plastic that allows sample access to the beads and using a confocal microscope for detection. Similarly, the beads may be placed on the inside surface of a tube, for flow-through sample analysis to minimize sample volume. Preferred substrates include optical fiber bundles as discussed below, and flat planar substrates, such as glass (e.g., flat glass coverslips), polystyrene and other plastics and acrylics.

At least one surface of the substrate is modified to contain discrete, individual sites for later association of microspheres. These sites may comprise physically altered sites, i.e., physical configurations such as wells or small depressions in the substrate that can retain the beads, such that a microsphere can rest in the well, or the use of other forces (magnetic or compressive), or chemically altered or active sites, such as chemically functionalized sites, electrostatically altered sites, hydrophobically/hydrophilically functionalized sites, spots of adhesive, etc.

The sites may be a pattern, i.e., a regular design or configuration, or randomly distributed. A preferred embodiment utilizes a regular pattern of sites such that the sites may be addressed in the X-Y coordinate plane. "Pattern" in this sense includes a repeating unit cell, preferably one that allows a high density of beads on the substrate. However, it should be noted that these sites may not be discrete sites. That is, it is possible to use a uniform surface of adhesive or chemical functionalities, for example, that allows the attachment of beads at any position. That is, the surface of the substrate is modified to allow attachment of the microspheres at individual sites, whether or not those sites are contiguous or non-contiguous with other sites. Thus, the surface of the substrate may be modified such that discrete sites are formed that can only have a single associated bead, or alternatively, the surface of the substrate is modified and beads may adhere anywhere, but they end up at discrete sites.

In certain embodiments, the surface of the substrate is modified to contain wells, i.e., depressions in the surface of the substrate. This may be done as is generally known in the art using a variety of techniques, including, but not limited to, photolithography, stamping techniques, molding techniques and microetching techniques. As will be appreciated by those in the art, the technique used will depend on the composition and shape of the substrate.

In a preferred embodiment, physical alterations are made in a surface of the substrate to produce the sites. In a preferred embodiment, the substrate is a fiber optic bundle and the surface of the substrate is a terminal end of the fiber bundle. In this embodiment, wells are made in a terminal or distal end of a fiber optic bundle comprising individual fibers. In this embodiment, the cores of the individual fibers are etched, with respect to the cladding, such that small wells or depressions are formed at one end of the fibers. The required depth of the wells will depend on the size of the beads to be added to the wells.

Generally in this embodiment, the microspheres are non-covalently associated in the wells, although the wells may additionally be chemically functionalized as is generally described below, cross-linking agents may be used, or a physical barrier may be used, i.e., a film or membrane over the beads.

In certain embodiments, the surface of the substrate is modified to contain chemically modified sites that can be used to attach, either covalently or non-covalently, the microspheres of the invention to the discrete sites or locations on the substrate. "Chemically modified sites" in this context includes, but is not limited to, the addition of a pattern of chemical functional groups including amino groups, carboxyl groups, oxo groups and thiol groups, that can be used to covalently attach microspheres, which generally also contain corresponding reactive functional groups; the addition of a pattern of adhesive that can be used to bind the microspheres (either by prior chemical functionalization for the addition of the adhesive or direct addition of the adhesive); the addition of a pattern of charged groups (similar to the chemical functionalities) for the electrostatic attachment of the microspheres, i.e., when the microspheres comprise charged groups opposite to the sites; the addition of a pattern of chemical functional groups that renders the sites differentially hydrophobic or hydrophilic, such that the addition of similarly hydrophobic or hydrophilic microspheres under suitable experimental conditions will result in association of the microspheres to the sites on the basis of hydroaffinity. For example, the use of hydrophobic sites with hydrophobic beads, in an aqueous system, drives the association of the beads preferentially onto the sites. As outlined above, "pattern" in this sense includes the use of a uniform treatment of the surface to allow attachment of the beads at discrete sites, as well as treatment of the surface resulting in discrete sites. As will be appreciated by those in the art, this may be accomplished in a variety of ways.

The compositions of the invention further comprise a population of microspheres. By "population" herein is meant a plurality of beads as outlined above for arrays. Within the population are separate subpopulations, which can be a single microsphere or multiple identical microspheres. That is, in some embodiments, as is more fully outlined below, the array may contain only a single bead for each analyte; preferred embodiments utilize a plurality of beads of each type.

Fluorescent Indicators

Certain embodiments of the invention related to fluorescent indicators with desired reactivity and fluorescence properties. In certain embodiments, fluoresceinamine (FLA), a commercially available fluorescent dye with reactivity for phosphonyl halides, or a FLA-analogue, is used to fabricate microbead sensors. Previous studies have demonstrated that FLA could be used as a turn-on fluorescent indicator. Munkholm, C.; Walt, D. R.; Milanovich, F. P.; Klainer, S. M. *Analytical Chemistry* 1986, 58, 1427-1430; and Munkholm, C.; Parkinson, D. R.; Walt, D. R. *Journal of the American Chemical Society* 1990, 112, 2608-2612. Remarkably, when FLA's amine group reacts with acyl and phosphonyl halides its quantum yield increases dramatically. This mechanism was observed as a 50-fold fluorescence increase (relative to the amine) upon reaction of FLA and acryloyl chloride.

Thus, FLA (FIG. 1, I) and its analogues are natural choices for a specific microbead phosphonyl halide probe because their reactivity is well established and the requisite form for sensing is commercially available. The size and geometry of the microbead sensors described here allow their inclusion into populations containing various cross-reactive sensors, such that they can be positioned on a microwell array and used as an early warning sentinel in conjunction with the optical electronic nose. Importantly, herein is disclosed that the FLA microbead probes respond within seconds of exposure to DCP and their fluorescence signal increase is stable.

In certain embodiments the fluorescent pre-exposure indicators of the invention have a structure represented by I or a salt thereof:

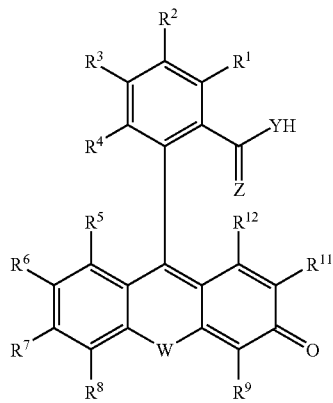

I wherein, independently for each occurrence, W is O, S, or $NR^A$; Y is O, S, or $NR^A$; Z is O, or $NRA^A$; $R^A$ is hydrogen, alkyl, acyl, or aralkyl; $R^1, R^2, R^3, R^4, R^5, R^6, R^7, R^8, R^9, R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and $—(CH_2)_m R^B$; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 1-10 inclusive; provided that at least one of $R^1, R^2, R^3$ and $R^4$ is $NH_2$.

Synthesis of Fluorescein Phosphamide (FLPA)

Fluorescein phosphamide (FLPA; FIG. 1, III) was first synthesized and isolated to establish the irreversible derivatization of FLA (I) with DCP (II). NMR characterization of the isolated product III validated the conversion to FLPA. According to $^1H$ NMR data the FLPA phenyl ring 2', 3', and 5' protons are deshielded relative to FLA protons (indicated in FIG. 1). Munkholm, C.; Parkinson, D. R.; Walt, D. R. *Journal of the American Chemical Society* 1990, 112, 2608-2612. These downfield shifts result from the electron withdrawal of the phosphamide and correlate with the previously observed NMR downfield proton shifts of the amides derived from FLA. In addition, the multiplet observed at 4.07 ppm indicates methylene splitting by both the methyl protons and the phosphorus.

Once the irreversible reaction between FLA and DCP was confirmed, the reactivity of FLA was tested in solution with several phosphonates to observe the specificity of the reaction. Finally, the interaction between the surface-immobilized indicator dye and DCP vapor were tested using FLA-coated microbeads with different microbead compositions including silica, polystyrene, and vinyl carboxylic acid/polystyrene copolymer microbeads with carboxylate surface groups covered with poly(2-vinylpyridine).

Phosphamide pH Dependence and Specificity

Based on previous interpretations, FLA is quenched relative to its acyl derivative because the lone pair nitrogen of the amine group quenches the fluorescence via photoinduced electron transfer (PET). Upon reaction with an acyl or phosphonyl group, the amino group's lone pair is less available and increased fluorescence is observed. This increased fluorescence in FLPA is attributed to the withdrawal of electrons from the phenyl ring by the phosphate double bonded oxygen. The electron density on the FLPA nitrogen and phenyl ring decreases, thereby increasing the fluorescence of the xanthene moiety in the FLPA molecule.

Figure 2:
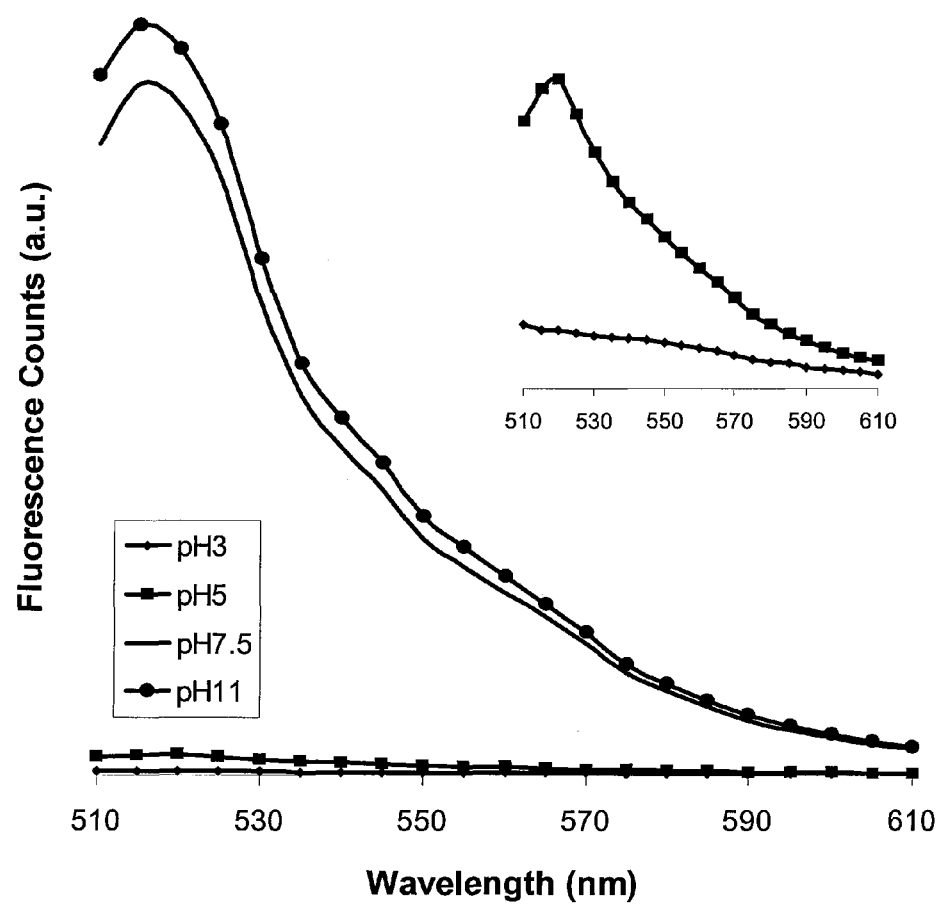
FIG. 2 depicts emission spectra of 0.5 mM FLPA in 0.05 M phosphate buffers with pH values 3.1, 5.0, 7.6, and 10.9 ($\lambda$ excitation=490 nm). The insert shows expanded emission spectra of the product in pH 3.1 and pH 5.0 buffers.

Fluorescein and its derivatives are known to exhibit strong pH dependence as evidenced by the fact that fluorescein is a useful pH indicator. Martin, M. M.; Lindqvist, L. *Journal of Luminescence* 1975, 10, 381-390. To verify pH sensitivity, fluorescence emission spectra of purified FLPA were acquired in different pH buffers and are shown in FIG. 2. Here, the fluorescence intensity of FLPA, observed at its emission maximum ($\lambda_{max}$=515 nm), was significantly higher than FLA fluorescence and increased from pH 7.5 to pH 11, whereas the fluorescence intensities in acidic buffers (pH 3 and 5) were several orders of magnitude lower. These emission spectra confirm that FLPA exhibits the highest fluorescence at pH above neutral.

Figure 3:
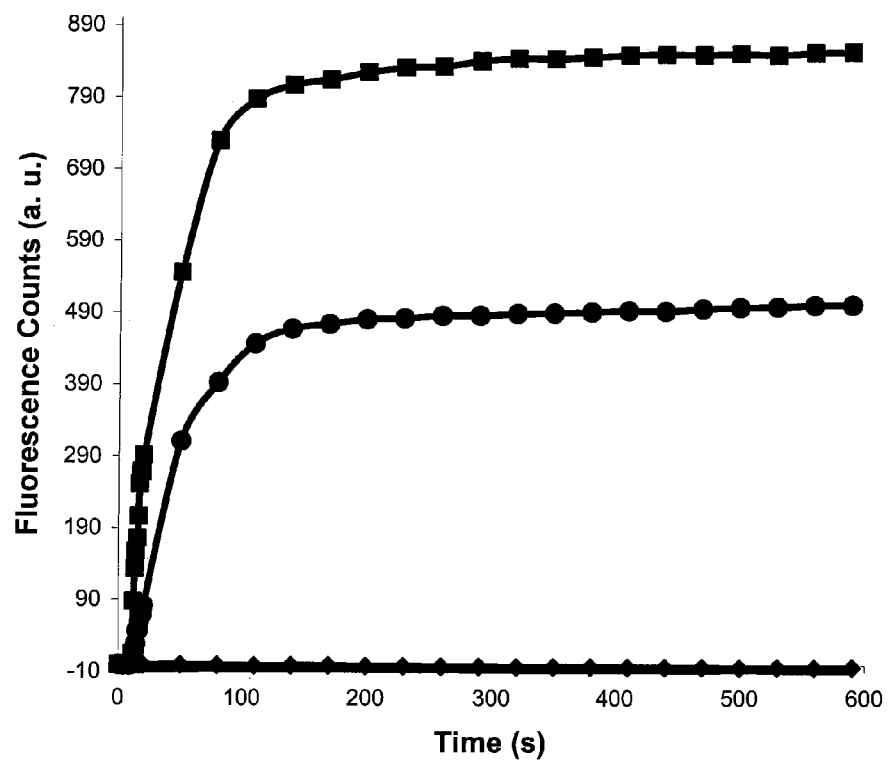
FIG. 3 depicts a baseline-subtracted fluorescence emission spectra of 1 mM FLA (in 0.05 M phosphate pH 7.5 buffer), monitored over time, after addition of 10-fold stoichiometric amounts of AC (squares), DCP (circles), DIMP (no symbol), and DMMP (diamonds) ($\lambda$ excitation=470 nm, $\lambda$ emission=530 nm). The analytes were introduced ten seconds after the beginning of data collection (see arrow in the bottom plot).
Figure 3:
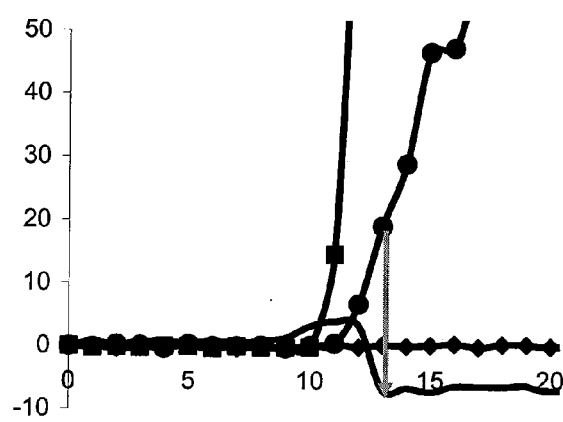

After optimizing the measurement pH, the turn-on behavior and FLA specificity for phosphonyl chloride were evaluated in solution. Four different reagents (AC, DCP, DIMP, and DMMP) were added to the FLA solution (pH 7.5) and the fluorescence intensity was measured over time. To perform these measurements in real time, a single-core optical fiber was immersed in the solution, and 10-fold stoichiometric amounts of AC, DCP, DIMP, and DMMP were injected by syringe following an initial 10-s baseline acquisition. FIG. 3 shows the fluorescence intensity of the solution, acquired through the optical fiber, during the various reactions. The insert shows the initial 30 s, indicating the time point when the reagents were injected. The additions of both AC and DCP resulted in increased fluorescence, which was attributed to amide and phosphamide formation, respectively. The fluorescence due to the amide formation was greater in both rate and magnitude. These differences were likely due to the different reactivities of carbonyl and phosphonyl halides. In theory, carbonyl chlorides like AC which contain a highly electron-withdrawing alkenyl group adjacent to the carbonyl should react much faster than phosphonyl chlorides which contain a weaker electron-withdrawing phosphonyl. Moreover, the higher reactivity of the $sp^2$ carbonyl arises also from the fact that the carbon is less sterically hindered than the highly-coordinated phosphorus. Despite the lower change in intensity, the increase in intensity confirmed the predicted turn-on behavior resulting from FLA derivatization with DCP. FLA specificity toward DCP was confirmed by monitoring the fluorescence of FLA mixed with non-reactive phosphonates (DIMP and DMMP). The fluorescence intensities of FLA mixtures with phosphonates without a halide reactive group did not change over time, indicating that these two simulants did not react with FLA.

These solution-based experiments demonstrate the specificity of FLA for phosphonyl halides and the intense fluorescence of the resulting phosphamide. The fluorescence increase obtained was due to careful solution pH control. These results were considered in the preparation of vapor-sensitive FLA-coated microbeads with turn-on behavior.

Responses of FLA-Coated Microbeads to DCP

The hydrochloric acid (HCl) that forms as a byproduct of the reaction between FLA and DCP could potentially cause a local decrease in pH, thereby quenching the FLPA adduct. By buffering the solution, HCl is neutralized. Maintaining the proper pH is more challenging when the reaction occurs in the solid state. With a solid phase reaction on microbeads, a proton sponge is required to maintain the microenvironment pH at a value where the FLPA remains highly fluorescent. FLPA quenching on the surface due to HCl was circumvented by preparing microbeads with surface groups that could neutralize the acid byproduct. To determine which microbead type would work best, FLA was adsorbed onto three different types of microbeads: silica (S), polystyrene (PS), and carboxylate-functionalized polystyrene (PSC). Surfaces of the first two microbead types were not modified, whereas the third microbead type was coated with a layer of poly(2-vinylpyridine) (PVP). PVP was chose due to its basicity (conjugate acid $pK_a$ of about 4). The PVP proton-accepting groups were expected to prevent acidification of FLPA. The surfaces of all the bead types were rinsed in buffer (pH 7.5) to convert FLA into its basic form and deprotonate the silica hydroxyl surface groups and poly(2-vinylpyridine) pyridine moieties. Ripoll, C.; Muller, G.; Selegny, E. *European Polymer Journal* 1971, 7, 1393-1409; Tao, Z.; Zhang, H. *Journal of Colloid and Interface Science* 2002, 252, 15-20.

Figure 4:
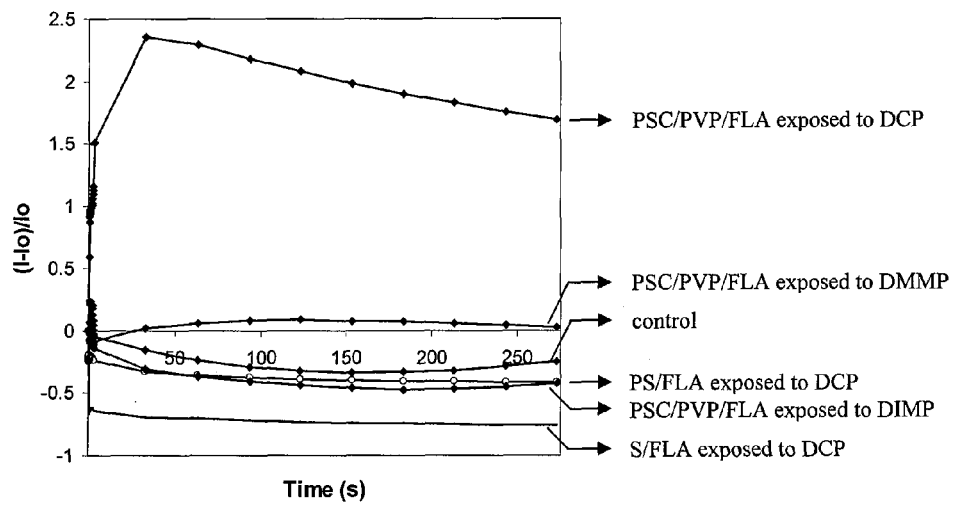
FIG. 4 depicts (A) a graph showing fluorescence responses of PSC/PVP/FLA (filled symbols), PS/FLA (open symbols), and S/FLA (no symbols) sensors during their exposure to 50% saturated DIMP, DMMP, or DCP; the control response (control) was acquired with PSC/PVP/FLA microbeads exposed to ambient air; and (B) a graph showing response shapes during the initial 10 seconds of acquisition (the duration of the pulse is indicated by the black bar).
Figure 4:
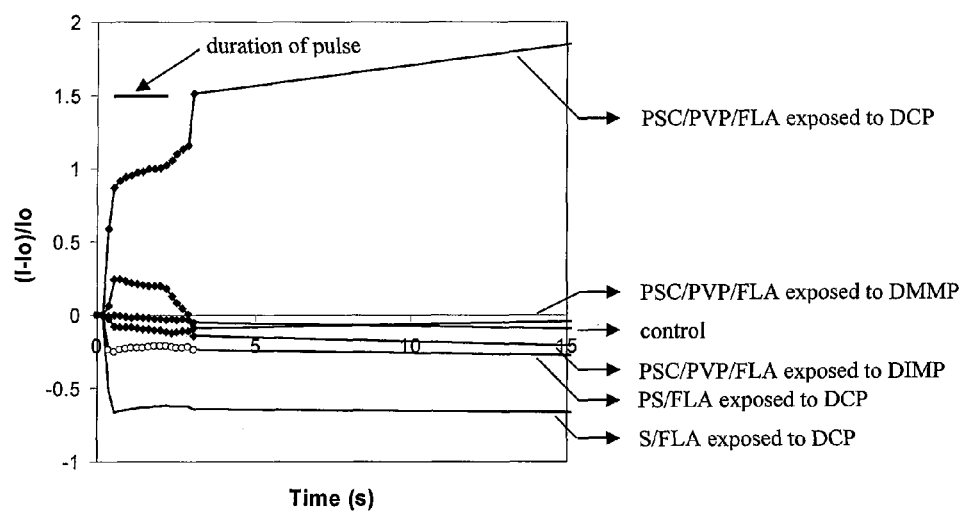

DCP vapor responses of the three microbead types (S/FLA, PS/FLA, and PSC/PVP/FLA) were acquired to determine which type would respond most rapidly and with the highest irreversible fluorescence increase. Each vapor response was acquired with a freshly prepared coverslip array, positioned on the optical microscope. The delivery of the vapors and the sequence in which the microbead types were inspected were randomized. DCP vapor responses of the three microbead types are shown in FIG. 4. Whereas S/FLA (no symbols) and PS/FLA (circles) microbeads did not turn on during exposure to 66 ppm DCP, the PSC/PVP/FLA microbeads (filled circles) exhibited a drastic fluorescence increase. The fluorescence intensity increase was highest (more than 200% increase) approximately 33 s after the vapor pulse and although it decreased slightly over time, the increase was larger than 150% even 4 minutes after vapor exposure. The largest fluorescence increase occurred after the pulse was discontinued. The increase in intensity during and after the vapor pulse (FIG. 4B) suggests that FLPA formed on the surface of the beads and that despite the HCl-induced quenching, the PVP layer effectively neutralized the acidic protons produced. The fluorescence of the S/FLA and PS/FLA microbeads decreased dramatically at the beginning of the DCP pulse and only slightly increased during the remainder of the exposure (FIG. 4B). The overall fluorescence was quenched after vapor exposure. This observation can be attributed to the buildup of HCl on the surface of the microbeads. Moreover, strong hydrogen bonding between the phosphonate molecules and hydroxyl groups on the silica surface likely occurred, which may have caused surface saturation with DCP and prevented the microbead surface from restoring to its initial condition and the dye returning to its unbleached state. Kanan, S. M.; Tripp, C. P. *Langmuir* 2001, 17, 2213-2218.

In addition to DCP vapor, the PSC/PVP/FLA microbeads were exposed to control vapors to confirm the specificity of the reaction between surface-bound FLA and vapor-phase DCP. The array was exposed to either 200 ppm DIMP or 1000 ppm DMMP (FIG. 4). As expected, the microbeads exposed to unreactive vapors did not turn on and their fluorescence changed only slightly over time. An additional control response that involved array exposure to air was acquired to determine whether the small change in fluorescence intensity over time originated from photobleaching. Although the fluorescence intensity of the array exposed to ambient air (shown in FIG. 4) somewhat decreased over time, the decrease may have been due to frequent changes in relative humidity surrounding the microbead probes, in addition to photobleaching. Humidity effects are discussed in more detail below.

Sensitivity and Microarray Response of PSC/PVP/FLA Microbeads

Figure 5:
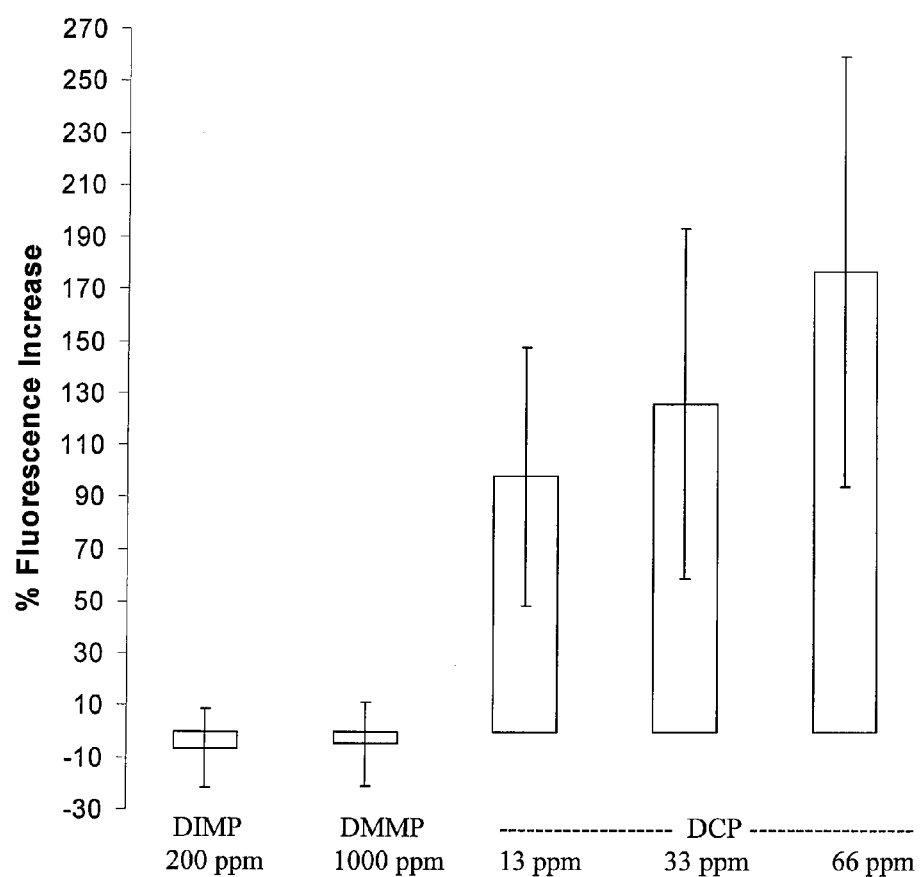
FIG. 5 depicts a bar graph showing a fluorescence percentage increase recorded 33 seconds after the beginning of the 1.6-second pulse. The values represented are the calculated averages and standard deviations of 50 PSC/PVP/FLA microbeads per array, selected randomly from individual arrays (N=8) and exposed to 200 ppm DIMP, 1000 ppm DMMP, or 13 ppm, 33 ppm, and 66 ppm DCP.
Figure 6:
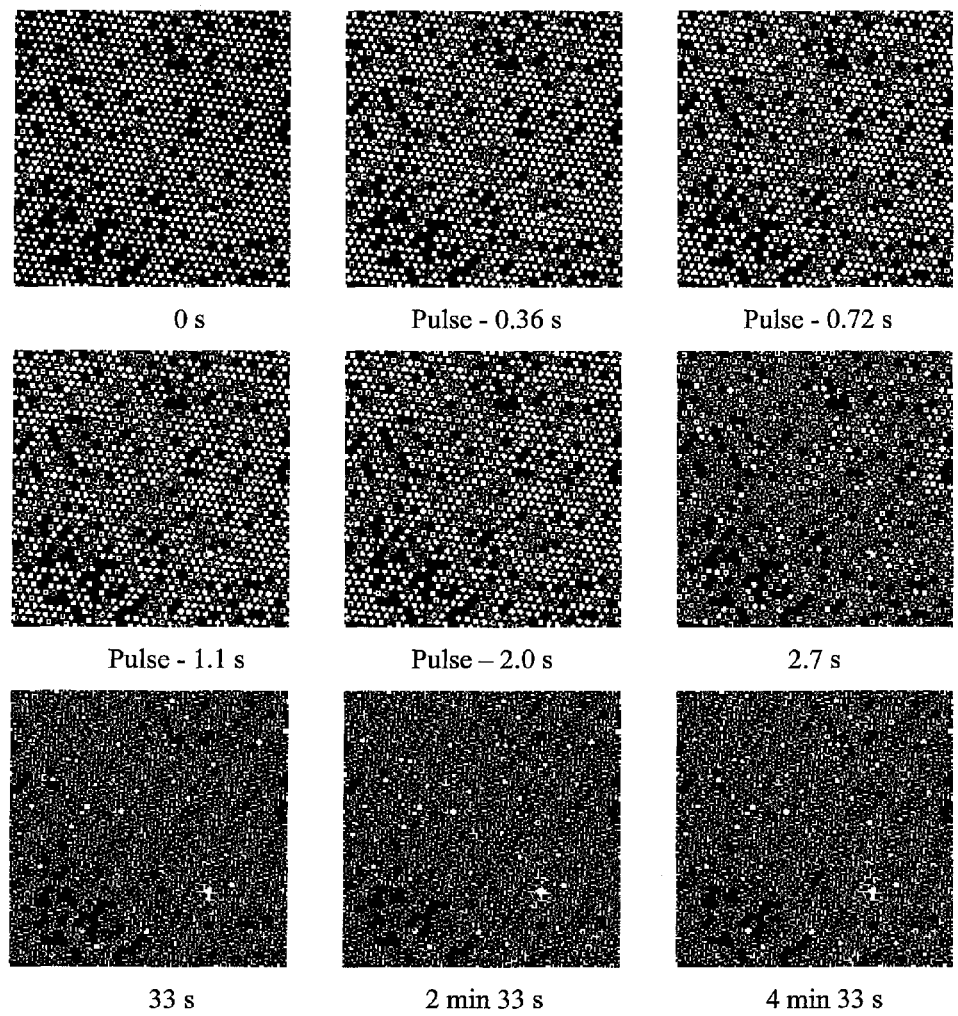
FIG. 6 depicts sequential images of an array of 4.5-$\mu$m wells filled with PSC/PVP/FLA microbeads that turn on irreversibly during and after a 1.6-second pulse of 66 ppm DCP vapor.
Figure 7:
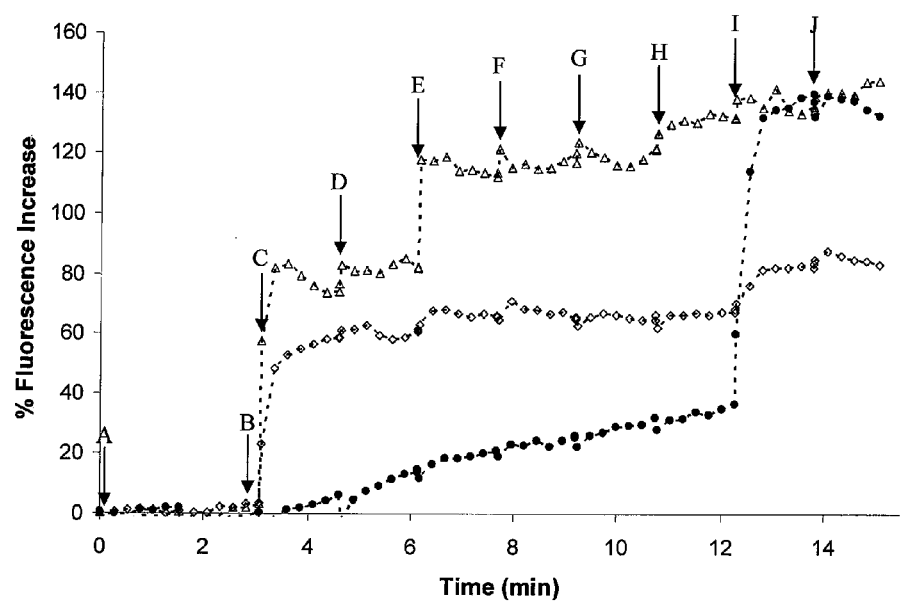
FIG. 7 depicts the averaged responses of 50 PSC/PVP/FLA sensors exposed to three different series of 50% saturated vapors. Each vapor was pulsed to the sensor array for 0.8 seconds and the resulting change of fluorescence intensity was recorded in 15-s intervals. The arrows indicate the beginning of each vapor pulse and correspond to the randomized vapor sequences (A-J) that are tabulated beneath the graph (DMMP is dimethyl methylphosphonate, DCP is diethyl chlorophosphate, and MS is methyl salicylate).

The sensitivity of the PSC/PVP/FLA microbeads was tested by exposing freshly prepared arrays to three different concentrations of DCP. 50% saturated DIMP and DMMP vapors were used as controls. FIG. 5 shows the percent increase in fluorescence intensities of 50-bead coverslip arrays. The fluorescence intensity values represented in the plot were measured 33 s after the beginning of a 1.6-s vapor pulse. Each of the five averaged intensities (13 ppm, 33 ppm, and 66 ppm DCP, 200 ppm DIMP, and 1000 ppm DMMP) was calculated using data from eight different arrays per vapor type, as each array was exposed only once to an individual vapor pulse because of the irreversible reaction. The intensities of microbeads exposed to DIMP and DMMP remained within baseline values and, as expected, microbead intensities increased with increasing DCP vapor concentration. Standard deviations of the three DCP averages were high (47 to 53%), likely due to the fact that each response was acquired with a different array. Despite the careful preparation of the microbeads coated with polymer and dye, the control of PVP and FLA adsorption on the bead surfaces was limited, thereby causing some non-homogenous surface coverage and a lower bead-to-bead reproducibility. When probes are designed more for alerting to the presence/absence of a harmful vapor exposure, quantitative measurements are less important than a measurable response. DCP detection is limited to low ppm levels with the microbead probes; therefore, for public safety, it may be necessary to blanket an area with sufficient sensors such that the time and level of exposure to a release are minimized. Moreover, because bulk agent will be needed to carry out an attack, ppm sensitivity should not be problematic.

To further demonstrate the feasibility of the PSC/PVP/FLA probes for use in array-based systems, the microbeads were positioned onto an array of microwells etched into an optical fiber bundle. A series of C In certain embodiments, the present invention relates to the aforementioned pre-exposure indicator and any of the attendant definitions, wherein Y is O.

In certain embodiments, the present invention relates to the aforementioned pre-exposure indicator and any of the attendant definitions, wherein Z is O.

In certain embodiments, the present invention relates to the aforementioned pre-exposure indicator and any of the attendant definitions, wherein Y is O; and Z is O.

In certain embodiments, the present invention relates to the aforementioned pre-exposure indicator and any of the attendant definitions, wherein $R^2$ is $NH_2$.

In certain embodiments, the present invention relates to the aforementioned pre-exposure indicator and any of the attendant definitions, wherein $R^1$ is H; $R^3$ is H; and $R^4$ is H.

In certain embodiments, the present invention relates to the aforementioned pre-exposure indicator and any of the attendant definitions, wherein $R^1$ is H; $R^2$ is $NH_2$; $R^3$ is H; and $R^4$ is H.

In certain embodiments, the present invention relates to the aforementioned pre-exposure indicator and any of the attendant definitions, wherein W is O.

In certain embodiments, the present invention relates to the aforementioned pre-exposure indicator and any of the attendant definitions, wherein $R^7$ is OH.

In certain embodiments, the present invention relates to the aforementioned pre-exposure indicator and any of the attendant definitions, wherein W is O; and $R^7$ is OH.

In certain embodiments, the present invention relates to the aforementioned pre-exposure indicator and any of the attendant definitions, wherein $R^5$ is H; $R^6$ is H; $R^8$ is H; $R^9$ is H; $R^{11}$ is H; and $R^{12}$ is H.

In certain embodiments, the present invention relates to the aforementioned pre-exposure indicator and any of the attendant definitions, wherein W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned pre-exposure indicator and any of the attendant definitions, wherein Y is O; Z is O; and $R^2$ is $NH_2$.

In certain embodiments, the present invention relates to the aforementioned pre-exposure indicator and any of the attendant definitions, wherein Y is O; Z is O; $R^1$ is H; $R^2$ is $NH_2$; $R^3$ is H; and $R^4$ is H.

In certain embodiments, the present invention relates to the aforementioned pre-exposure indicator and any of the attendant definitions, wherein Y is O; Z is O; and W is O.

In certain embodiments, the present invention relates to the aforementioned pre-exposure indicator and any of the attendant definitions, wherein Y is O; Z is O; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned pre-exposure indicator and any of the attendant definitions, wherein $R^1$ is H; $R^2$ is $NH_2$; $R^3$ is H; $R^4$ is H; and W is O.

In certain embodiments, the present invention relates to the aforementioned pre-exposure indicator and any of the attendant definitions, wherein $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned pre-exposure indicator and any of the attendant definitions, wherein Y is O; Z is O; $R^2$ is $NH_2$; and $R^7$ is OH.

In certain embodiments, the present invention relates to the aforementioned pre-exposure indicator and any of the attendant definitions, wherein Y is O; Z is O; $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

Selected Microbeads of the Invention

One aspect of the invention relates to a microbead comprising a fluorescent pre-exposure indicator, wherein said fluorescent pre-exposure indicator is represented by I or a salt thereof:

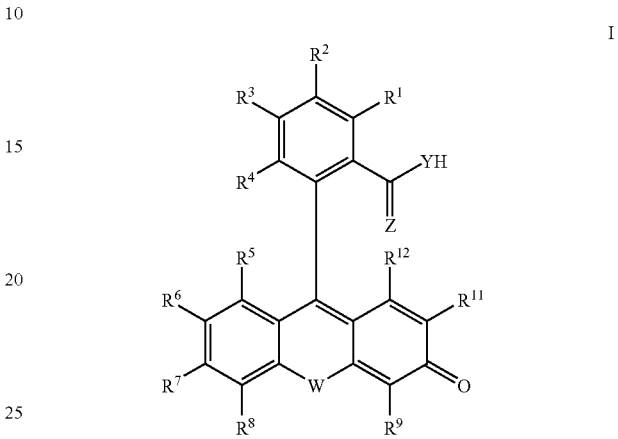

I wherein, independently for each occurrence, W is O, S, or $NR^A$; Y is O, S, or $NR^A$; Z is O, or $NR^A$; $R^A$ is hydrogen, alkyl, acyl, or aralkyl; $R^1$, $R^2$, $R^3$, $R^4$, $R^5$, $R^6$, $R^7$, $R^8$, $R^9$, $R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and $-(CH_2)_m R^B$; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 1-10 inclusive; provided that at least one of $R^1$, $R^2$, $R^3$ and $R^4$ is $NH_2$.

In certain embodiments, the present invention relates to the aforementioned microbead and any of the attendant definitions, wherein Y is O.

In certain embodiments, the present invention relates to the aforementioned microbead and any of the attendant definitions, wherein Z is O.

In certain embodiments, the present invention relates to the aforementioned microbead and any of the attendant definitions, wherein Y is O; and Z is O.

In certain embodiments, the present invention relates to the aforementioned microbead and any of the attendant definitions, wherein $R^2$ is $NH_2$.

In certain embodiments, the present invention relates to the aforementioned microbead and any of the attendant definitions, wherein $R^1$ is H; $R^3$ is H; and $R^4$ is H.

In certain embodiments, the present invention relates to the aforementioned microbead and any of the attendant definitions, wherein $R^1$ is H; $R^2$ is $NH_2$; $R^3$ is H; and $R^4$ is H.

In certain embodiments, the present invention relates to the aforementioned microbead and any of the attendant definitions, wherein W is O.

In certain embodiments, the present invention relates to the aforementioned microbead and any of the attendant definitions, wherein $R^7$ is OH.

In certain embodiments, the present invention relates to the aforementioned microbead and any of the attendant definitions, wherein W is O; and $R^7$ is OH.

In certain embodiments, the present invention relates to the aforementioned microbead and any of the attendant definitions, wherein $R^5$ is H; $R^6$ is H; $R^8$ is H; $R^9$ is H; $R^{11}$ is H; and $R^{12}$ is H.

In certain embodiments, the present invention relates to the aforementioned microbead and any of the attendant definitions, wherein W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned microbead and any of the attendant definitions, wherein Y is O; Z is O; and $R^2$ is $NH_2$.

In certain embodiments, the present invention relates to the aforementioned microbead and any of the attendant definitions, wherein Y is O; Z is O; $R^1$ is H; $R^2$ is $NH_2$; $R^3$ is H; and $R^4$ is H.

In certain embodiments, the present invention relates to the aforementioned microbead and any of the attendant definitions, wherein Y is O; Z is O; and W is O.

In certain embodiments, the present invention relates to the aforementioned microbead and any of the attendant definitions, wherein Y is O; Z is O; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned microbead and any of the attendant definitions, wherein $R^1$ is H; $R^2$ is $NH_2$; $R^3$ is H; $R^4$ is H; and W is O.

In certain embodiments, the present invention relates to the aforementioned microbead and any of the attendant definitions, wherein $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned microbead and any of the attendant definitions, wherein Y is O; Z is O; $R^2$ is $NH_2$; and $R^7$ is OH.

In certain embodiments, the present invention relates to the aforementioned microbead and any of the attendant definitions, wherein Y is O; Z is O; $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned microbead and any of the attendant definitions, wherein said indicator is bonded to the microbead.

In certain embodiments, the present invention relates to the aforementioned microbead and any of the attendant definitions, wherein said indicator is absorbed on the microbead.

In certain embodiments, the present invention relates to the aforementioned microbead and any of the attendant definitions, wherein said microbead consists essentially of plastic, ceramic, glass, polystyrene, methylstyrene, acrylic, paramagnetic, thoria sol, carbon graphite, titanium dioxide, latex cross-linked dextrans, Sepharose, cellulose, nylon, cross-linked micelles or Teflon.

In certain embodiments, the present invention relates to the aforementioned microbead and any of the attendant definitions, wherein said microbead consists essentially of silica, poly(ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80-85%) dimethyl-(15-20%) (acryloxypropyl)methylsiloxane copolymer], PS901.5 [poly(acryloxypropyl-methyl)siloxane], PS851 [(97-98%) dimethyl-(2-3%) (methacryloxypropyl)methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, an acrylic polymer, or poly(methyl styrene/divinyl benzene).

In certain embodiments, the present invention relates to the aforementioned microbead and any of the attendant definitions, wherein said microbead consists essentially of polystyrene.

Selected Methods of the Invention

One aspect of the invention relates to a method of detecting an analyte comprising the steps of exposing a pre-exposure indicator to a sample optionally comprising an analyte, thereby providing a post-exposure indicator; exposing said post-exposure indicator to light at a first wavelength; measuring the fluorescence of the post-exposure indicator at a second wavelength; and comparing the fluorescence of the post-exposure indicator at the second wavelength to the fluorescence of the pre-exposure indicator at the second wavelength; wherein said pre-exposure indicator is represented by structure I or a salt thereof:

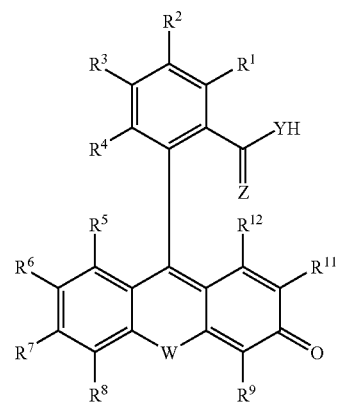

wherein, independently for each occurrence, W is O, S, or $NR^A$; Y is O, S, or $NR^A$; Z is O, or $NR^A$; $R^A$ is hydrogen, alkyl, acyl, or aralkyl; $R^1$, $R^2$, $R^3$, $R^4$, $R^5$, $R^6$, $R^7$, $R^8$, $R^9$, $R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and $—(CH_2)_mR^B$; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 1-10 inclusive; provided that at least one of $R^1$, $R^2$, $R^3$ and $R^4$ is $NH_2$.

In certain embodiments, the present invention relates to the aforementioned method and any of the attendant definitions, wherein said indicator is bonded to a microbead.

In certain embodiments, the present invention relates to the aforementioned method and any of the attendant definitions, wherein said indicator is absorbed on a microbead.

In certain embodiments, the present invention relates to the aforementioned method and any of the attendant definitions, wherein Y is O.

In certain embodiments, the present invention relates to the aforementioned method and any of the attendant definitions, wherein Z is O.

In certain embodiments, the present invention relates to the aforementioned method and any of the attendant definitions, wherein Y is O; and Z is O.

In certain embodiments, the present invention relates to the aforementioned method and any of the attendant definitions, wherein $R^2$ is $NH_2$.

In certain embodiments, the present invention relates to the aforementioned method and any of the attendant definitions, wherein $R^1$ is H; $R^3$ is H; and $R^4$ is H.

In certain embodiments, the present invention relates to the aforementioned method and any of the attendant definitions, wherein $R^1$ is H; $R^2$ is $NH_2$; $R^3$ is H; and $R^4$ is H.

In certain embodiments, the present invention relates to the aforementioned method and any of the attendant definitions, wherein W is O.

In certain embodiments, the present invention relates to the aforementioned method and any of the attendant definitions, wherein $R^7$ is OH.

In certain embodiments, the present invention relates to the aforementioned method and any of the attendant definitions, wherein W is O; and $R^7$ is OH.

In certain embodiments, the present invention relates to the aforementioned method and any of the attendant definitions, wherein $R^5$ is H; $R^6$ is H; $R^8$ is H; $R^9$ is H; $R^{11}$ is H; and $R^{12}$ is H.

In certain embodiments, the present invention relates to the aforementioned method and any of the attendant definitions, wherein W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned method and any of the attendant definitions, wherein Y is O; Z is O; and $R^2$ is $NH_2$.

In certain embodiments, the present invention relates to the aforementioned method and any of the attendant definitions, wherein Y is O; Z is O; $R^1$ is H; $R^2$ is $NH_2$; $R^3$ is H; and $R^4$ is H.

In certain embodiments, the present invention relates to the aforementioned method and any of the attendant definitions, wherein Y is O; Z is O; and W is O.

In certain embodiments, the present invention relates to the aforementioned method and any of the attendant definitions, wherein Y is O; Z is O; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned method and any of the attendant definitions, wherein $R^1$ is H; $R^2$ is $NH_2$; $R^3$ is H; $R^4$ is H; and W is O.

In certain embodiments, the present invention relates to the aforementioned method and any of the attendant definitions, wherein $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned method and any of the attendant definitions, wherein Y is O; Z is O; $R^2$ is $NH_2$; and $R^7$ is OH.

In certain embodiments, the present invention relates to the aforementioned method and any of the attendant definitions, wherein Y is O; Z is O; $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned method and any of the attendant definitions, wherein said analyte is represented by structure C:

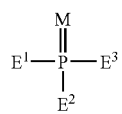

wherein, independently for each occurrence, M is O, S, or $NR^A$; $R^A$ is hydrogen, alkyl, acyl, or aralkyl; $E^1$ is F, Cl, Br or I; $E^2$ is hydroxyl, alkoxy, aryloxy, aralkoxy, acyloxy, thio, sulfonyl, sulfhydryl, sulfamoyl, sulfonamido, sulfate, sulfonate, sulfoxido, amino, imino, amido, trifluoroalkyl, cyano, $-O(CH_2)_mR^B$, $-NH(CH_2)_mR^B$, $-S(CH_2)_mR^B$; $E^3$ is hydrogen, alkyl, cycloalkyl, heterocycloalkyl, alkenyl, alkynyl, aryl, heteroaryl, aralkyl, heteroaralkyl, hydroxyl, alkoxy, aryloxy, aralkoxy, acyloxy, thio, sulfonyl, sulfhydryl, sulfamoyl, sulfonamido, sulfate, sulfonate, sulfoxido, amino, imino, amido, trifluoroalkyl, or cyano; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 0-10 inclusive.

In certain embodiments, the present invention relates to the aforementioned method and any of the attendant definitions, wherein $E^1$ is F.

In certain embodiments, the present invention relates to the aforementioned method and any of the attendant definitions, wherein $E^1$ is Cl.

In certain embodiments, the present invention relates to the aforementioned method and any of the attendant definitions, wherein $E^2$ is alkoxy, amino, thio, $-O(CH_2)_mR^B$, $-NH(CH_2)_mR^B$, or $-S(CH_2)_mR^B$.

In certain embodiments, the present invention relates to the aforementioned method and any of the attendant definitions, wherein $E^2$ is ethoxy.

In certain embodiments, the present invention relates to the aforementioned method and any of the attendant definitions, wherein $E^3$ is alkyl, cycloalkyl, or alkoxy.

In certain embodiments, the present invention relates to the aforementioned method and any of the attendant definitions, wherein $E^3$ is methyl, ethyl, propyl, isopropyl, butyl, isobutyl, pentyl, isopentyl, 1,2,2-trimethylpropyl, cyclopentyl, cyclohexyl, cycloheptyl, or cyclohexenyl.

In certain embodiments, the present invention relates to the aforementioned method and any of the attendant definitions, wherein $E^3$ is methyl.

In certain embodiments, the present invention relates to the aforementioned method and any of the attendant definitions, wherein said analyte is selected from the group consisting of tabun (GA), sarin (GB), soman (GD), and cyclosarin (GF), phosgene, O-ethyl S-(2-diisopropylaminoethyl)methylphosphonothioate (VX), diethyl chlorophosphate (DCP) and thionyl chloride.

In certain embodiments, the present invention relates to the aforementioned method and any of the attendant definitions, wherein said microbead consists essentially of plastic, ceramic, glass, polystyrene, methylstyrene, acrylic, paramagnetic, thoria sol, carbon graphite, titanium dioxide, latex cross-linked dextrans, Sepharose, cellulose, nylon, cross-linked micelles or Teflon®.

In certain embodiments, the present invention relates to the aforementioned method and any of the attendant definitions, wherein said microbead consists essentially of silica, poly (ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80-85%) dimethyl-(15-20%) (acryloxypropyl)methylsiloxane copolymer], PS901.5 [poly (acryloxypropyl-methyl)siloxane], PS851 [(97-98%) dimethyl-(2-3%) (methacryloxypropyl)methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, an acrylic polymer, or poly(methyl styrene/divinyl benzene).

In certain embodiments, the present invention relates to the aforementioned method and any of the attendant definitions, wherein said microbead consists essentially of polystyrene.

In certain embodiments, the present invention relates to the aforementioned method and any of the attendant definitions, wherein said first wavelength is about 490 nm.

In certain embodiments, the present invention relates to the aforementioned method and any of the attendant definitions, wherein said second wavelength is between about 510 nm and about 610 nm.

Selected Sensors of the Invention

Another aspect of the invention relates to an optical sensor comprising, an optical array comprising a plurality of pre-exposure indicators immobilized on a supporting member; wherein said pre-exposure indicator is represented by structure I or a salt thereof:

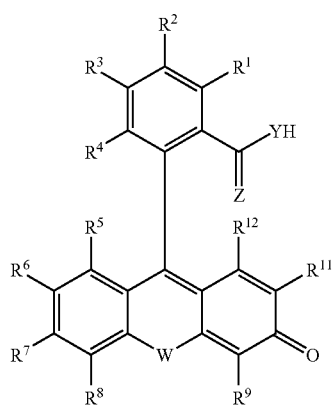

I wherein, independently for each occurrence, W is O, S, or $NR^A$; Y is O, S, or $NR^A$; Z is O, or $NR^A$; $R^A$ is hydrogen, alkyl, acyl, or aralkyl; $R^1$, $R^2$, $R^3$, $R^4$, $R^5$, $R^6$, $R^7$, $R^8$, $R^9$, $R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and —$(CH_2)_m R^B$; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 1-10 inclusive; provided that at least one of $R^1$, $R^2$, $R^3$ and $R^4$ is $NH_2$.

In certain embodiments, the present invention relates to the aforementioned sensor and any of the attendant definitions, wherein at least one of said plurality of indicators is bonded to a microbeads.

In certain embodiments, the present invention relates to the aforementioned sensor and any of the attendant definitions, wherein at least one of said plurality of indicators is absorbed on a microbeads.

In certain embodiments, the present invention relates to the aforementioned sensor and any of the attendant definitions, wherein Y is O.

In certain embodiments, the present invention relates to the aforementioned sensor and any of the attendant definitions, wherein Z is O.

In certain embodiments, the present invention relates to the aforementioned sensor and any of the attendant definitions, wherein Y is O; and Z is O.

In certain embodiments, the present invention relates to the aforementioned sensor and any of the attendant definitions, wherein $R^2$ is $NH_2$.

In certain embodiments, the present invention relates to the aforementioned sensor and any of the attendant definitions, wherein $R^1$ is H; $R^3$ is H; and $R^4$ is H.

In certain embodiments, the present invention relates to the aforementioned sensor and any of the attendant definitions, wherein $R^1$ is H; $R^2$ is $NH_2$; $R^3$ is H; and $R^4$ is H.

In certain embodiments, the present invention relates to the aforementioned sensor and any of the attendant definitions, wherein W is O.

In certain embodiments, the present invention relates to the aforementioned sensor and any of the attendant definitions, wherein $R^7$ is OH.

In certain embodiments, the present invention relates to the aforementioned sensor and any of the attendant definitions, wherein W is O; and $R^7$ is —OH.

In certain embodiments, the present invention relates to the aforementioned sensor and any of the attendant definitions, wherein $R^5$ is H; $R^6$ is H; $R^8$ is H; $R^9$ is H; $R^{11}$ is H; and $R^{12}$ is H.

In certain embodiments, the present invention relates to the aforementioned sensor and any of the attendant definitions, wherein W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned sensor and any of the attendant definitions, wherein Y is O; Z is O; and $R^2$ is $NH_2$.

In certain embodiments, the present invention relates to the aforementioned sensor and any of the attendant definitions, wherein Y is O; Z is O; $R^1$ is H; $R^2$ is $NH_2$; $R^3$ is H; and $R^4$ is H.

In certain embodiments, the present invention relates to the aforementioned sensor and any of the attendant definitions, wherein Y is O; Z is O; and W is O.

In certain embodiments, the present invention relates to the aforementioned sensor and any of the attendant definitions, wherein Y is O; Z is O; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned sensor and any of the attendant definitions, wherein $R^1$ is H; $R^2$ is $NH_2$; $R^3$ is H; $R^4$ is H; and W is O.

In certain embodiments, the present invention relates to the aforementioned sensor and any of the attendant definitions, wherein $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned sensor and any of the attendant definitions, wherein Y is O; Z is O; $R^2$ is $NH_2$; and $R^7$ is OH.

In certain embodiments, the present invention relates to the aforementioned sensor and any of the attendant definitions, wherein Y is O; Z is O; $R^1$ is H; $R^2$ is $NH_2$; $R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

In certain embodiments, the present invention relates to the aforementioned sensor and any of the attendant definitions, wherein said microbeads consist essentially of plastic, ceramic, glass, polystyrene, methylstyrene, acrylic, paramagnetic, thoria sol, carbon graphite, titanium dioxide, latex cross-linked dextrans, Sepharose, cellulose, nylon, cross-linked micelles or Teflon.

In certain embodiments, the present invention relates to the aforementioned sensor and any of the attendant definitions, wherein said microbeads consist essentially of silica, poly (ethylene glycol), polycaprolactone, poly(1,4-butylene adipate), PDPO [poly(2,6-dimethyl-1,4-phenyleneoxide)], PS078.5 [triethoxysilyl-modified polybutadiene (50% in toluene)], PS078.8 [diethoxymethylsilyl-modified polybutadiene in toluene], CPS2067 [acryloxypropylmethyl-cyclosiloxane], PS802 [(80-85%) dimethyl-(15-20%) (acryloxypropyl)methylsiloxane copolymer], PS901.5 [poly (acryloxypropyl-methyl)siloxane], PS851 [(97-98%) dimethyl-(2-3%) (methacryloxypropyl)methylsiloxane copolymer], PABS [poly(acrylonitrile-butadiene-styrene)], poly(methyl methacrylate), poly(styrene-acrylonitrile 75:25), acryloxypropylmethylsiloxane-dimethylsiloxane copolymer, methylstyrene, polystyrene, acrylic polymers, or poly(methyl styrene/divinyl benzene).

In certain embodiments, the present invention relates to the aforementioned sensor and any of the attendant definitions, wherein said microbeads consist essentially of polystyrene.

In certain embodiments, the present invention relates to the aforementioned sensor and any of the attendant definitions, wherein said supporting member is glass, modified or functionalized glass, plastic, an acrylic, polystyrene, a styrene-containing copolymer, polypropylene, polyethylene, polybutylene, a polyurethane, Teflon, a polysaccharide, nylon, nitrocellulose, a resin, silica, a silica-based material, modified silicon, carbon, a metal, or an optical fiber bundle. In certain embodiments, the present invention relates to the aforementioned sensor and any of the attendant definitions, where said supporting member is glass.

EXEMPLIFICATION

The invention now being generally described, it will be more readily understood by reference to the following examples, which are included merely for purposes of illustration of certain aspects and embodiments of the present invention, and are not intended to limit the invention.

Example 1

Materials and Instrumental Setup

Fluoresceinamine (Isomer I), ethanol, potassium phosphate monobasic solution (1M), potassium phosphate dibasic solution (1M), hydrochloric acid, sodium hydroxide, acryloyl chloride, diethyl chlorophosphate, dimethyl methylphosphonate, and poly(2-vinylpyridine) (secondary standard; $M_w$=37,500, $M_n$=35,000) were purchased from Aldrich (Milwaukee, Wis.) and used as received. Diisopropyl methylphosphonate (DIMP) was purchased from Lancaster Synthesis (Lancashire, UK). Silica microbeads (3-μm diameter) were retrieved from a Luna Silica (2) liquid chromatography column (Phenomenex, Torrance, Calif.), washed with toluene and dried at 60° C. overnight. Polystyrene (PS05N, 2.93 μm diameter, water suspension, 10% solids) and carboxylate-modified polystyrene (PC05N, 3.20 μm diameter, water suspension, 10% solids) microbead suspensions in water were purchased from Bangs Laboratories (Fishers, Ind.). Glass coverslips (30-mm diameter) were purchased from ProSciTech (Queensland, Australia). Optical fiber bundles with 4.5-μm diameter wells, used in the preparation of microbead arrays, were purchased from Illumina, Inc. (San Diego, Calif.).

$^1$H NMR spectra were recorded on a Bruker AM-300 spectrometer. Chemical shifts were measured relative to the solvent peaks (DMSO-$d_6$ 2.50 ppm relative to TMS). ESI-MS spectra were acquired with a Finnigan LTQ spectrometer (Thermo Electron Corporation, Waltham, Mass.). Fluorescence emission spectra were acquired with a SpectraMax Gemini microplate spectrofluorometer (Sunnyvale, Calif.). Fluorescence measurements in solution and vapor responses were acquired with a fluorescence imaging system, slightly modified with respect to a previously described one. Stitzel, S. E.; Cowen, L. J.; Albert, K. J.; Walt, D. R. *Analytical Chemistry* 2001, 73, 5266-5271. In brief, the system comprised a BX Olympus horizontal microscope (Melville, N.Y.), automated excitation and emission filter wheels, a 75 W Xenon excitation source (Ludl, Hawthorne, N.Y.), and a Sensicam QE (1376×1040 pixel) CCD Camera (Cooke Corp., Auburn Hills, Mich.). Additional optics included a 20× objective, 1.6× and 0.5× optical lenses, and several neutral density filters. 4×4 binning was employed in all measurements.

Example 2

Synthesis of Fluorescein Phosphamide

A dry system that consisted of a reaction flask connected to a condenser with a $CaCl_2$-filled tube was used for the synthesis of the phosphamide product. Fluoresceinamine (50 mg; 0.14 mmol) was first dissolved in 1.5 mL acetone to form a yellow solution. The solution color changed to orange upon addition of diethyl chlorophosphate (25 μL; 0.17 mmol). The reaction mixture was stirred at room temperature for 48 h until the fluorescein phosphamide (FLPA) precipitated. Subsequent vacuum filtration and multiple acetone rinses were followed by evaporation to recover the product (orange powder), which was characterized by $^1$H NMR and MS: $^1$H NMR δ 1.26 (t, 6H, J=7.02 Hz, $CH_3$), 4.07 (m, 4H, $OCH_2$), 6.57 (m, 4H, $H_2$, $H_3$), 6.66 (s, 2H, $H_5$), 7.12 (d, 1H, J=8.5 Hz, $H_{2'}$), 7.4 (dd, 1H, $J_1$=8.16 Hz, $J_2$=1.9 Hz, $H_{3'}$), 7.51 (d, 1H, J=1.7 Hz, $H_{5'}$), 8.61 (d, 1H, J=9.10, NH), 10.1 (br, 1H, OH); exact mass calculated for $C_{24}H_{22}NO_8P+H^+$: 484.12. found 484.06.

Example 3

Preparation of Silica-FLA Beads

Silica (S) microbeads (15 mg) were mixed with 1.5 mL of 1 mM fluoresceinamine in 0.05 M phosphate buffer (pH 7.5) for 2 hours, filtered and washed with buffer and dried at 60° C. overnight.

Example 4

Preparation of Polymer-FLA Beads

200-μL aliquots of polystyrene microbeads (PS) and vinyl carboxylic acid/polystyrene copolymer microbeads with carboxylate surface groups (PSC) were washed separately three times with 0.5 mL ethanol by centrifugation and removal of the supernatant. The microbeads were resuspended in 0.5-mL ethanol by 2-min sonication. Both bead suspensions were then placed in 4-mL sealed amber vials, equipped with stir bars. A 0.5-mL aliquot of 0.4 M (monomer concentration) poly(2-vinylpyridine) (PVP) in ethanol was added dropwise to the stirred PSC bead suspension and the mixture was stirred for an additional 30 minutes. PVP was added first to ensure electrostatic binding of the positively charged PVP amines to carboxylate-functionalized microbead surfaces prior to fluoresceinamine addition. Fluoresceinamine (0.5 mL, 10 mg/mL in ethanol) was then added dropwise to the PS microbead suspension and to the PSC microbeads coated with PVP. After 2 hours of continuous stirring, both bead stocks were filtered with a conventional filtration setup equipped with a 25-mm diameter 0.45-μm pore size HVLP filter (Millipore), and washed with two 0.5-mL aliquots of 0.05 M phosphate buffer (pH 7.5). The microbeads were dried at 60° C. for 1 hour.

Example 5

Preparation of Microbead Arrays

Coverslip arrays and fiber bundle arrays were prepared as described previously. Stitzel, S. E.; Cowen, L. J.; Albert, K. J.; Walt, D. R. *Analytical Chemistry* 2001, 73, 5266-5271; and Bencic-Nagale, S.; Walt, D. R. *Analytical Chemistry* 2005, 77, 6155-6162. Each vapor response was acquired with a new coverslip array, prepared by smearing a small portion of the microbead stock onto a glass coverslip.

Example 6

Fluorescence Measurements

FLA solution (0.5 mM) was prepared by dissolving fluoresceinamine in 0.05 M phosphate buffer (pH 7.5). The 0.05 M phosphate buffer solutions with pH 3.1, 5.0, and 10.9 were prepared by adding concentrated HCl or NaOH to the pH 7.5 buffer to achieve the desired pH. The 0.5 mM solutions of FLPA were prepared by diluting a 10 mM ethanolic solution of FLPA with the four phosphate buffers. Fluorescence emission spectra were acquired with a microplate spectrofluorometer at 490 nm excitation and emission between 510 nm and 610 nm using a 5-nm wavelength step.

Example 7

Solution Testing

A single-core optical fiber coupled to the imaging system was used to monitor the changes in fluorescence occurring when AC, DCP, DIMP, and DMMP were added to the FLA solution. Excitation light (470 nm) was passed through the fiber and the average emission intensity (550 nm) of a region on the proximal fiber end was measured with the CCD camera. The 370-μm diameter single-core optical fiber used in the experiment was first polished using a series of lapping films (30 μm, 12 μm, 3 μm, and 0.3 μm; Mark V Laboratories, East Granby, Conn.), rinsed with deionized water and immersed into a 4-mL vial equipped with a stir bar. 2 mL of 1 mM FLA solution were first pipetted into each vial and 2 μL, 3 μL, 2 μL, and 3 μL of AC, DIMP, DMMP, and DCP, respectively, were injected with a disposable syringe (Fisher Scientific) during constant stirring to achieve a ~10-fold stoichiometric amount of each reactant in solution. The first 20 data points were acquired in 1-s intervals. Each reagent was injected into the FLA solution immediately after the acquisition of the $10^{th}$ data point. After the rapid data acquisition during the injection of the analytes in the beginning of the experiment, an additional 20 data points were acquired in 30-s intervals. The resulting overall experimental time was 620 s.

Example 8

Collection of Vapor Responses

Vapor responses were acquired using coverslip arrays imaged by the fluorescence imaging system. The microbeads were excited at 470 nm and their responses were monitored at 550 nm emission wavelength. Saturated vapors, mixed with ultra-zero-grade air to yield different vapor concentrations, were prepared with an automated vapor delivery system (GDS, Orono, Me.) described in detail elsewhere. Bencic-Nagale, S.; Walt, D. R. *Analytical Chemistry* 2005, 77, 6155-6162. In brief, saturated vapor of each analyte was prepared by passing air through liquid placed in a sealed bubbler. The desired concentrations of vapors were achieved by adjusting the percentages of saturated vapor and air flow rates, keeping the total flow at 200 mL/min (FIG. 8). The vapor delivery lines were purged with each vapor mixture for 45 s before the vapor was delivered to the array. The concentration of the headspace vapor was held constant by keeping the bubblers at 25° C.

Each 27-frame vapor response movie consisted of 17 100-ms fast-capture frames (2 baseline frames, 10 frames collected during the vapor pulse, 5 frames collected after the pulse), and an additional 10 frames collected 30 seconds apart. The vapor pulse was 1.6 s long. After a vapor response had been acquired, the vapor delivery system lines were flushed with air for 2.5 min (200 mL/min) and a new coverslip array was positioned on the microscope before acquiring a new vapor response. The long purging of the vapor delivery tubing with air prevented any residues of previously used vapors from contaminating each newly-prepared vapor mixture. For the 10 vapor sequences, a similar acquisition protocol was acquired as for the individual vapor responses. After 12 100-ms exposures (2 baseline frames, 5 pulse frames, and 5 frames following the pulse), 10 more frames were recorded in 15-s intervals. Each vapor pulse lasted 0.8 seconds. Once the 22 frames were acquired with the first vapor, the same data acquisition scheme was repeated for the next vapor and for each subsequent vapor in the sequence. The gas delivery lines were flushed with air for 10 minutes after each 10-vapor sequence. All vapor experiments were performed between 21-25° C. and between 21-50% relative humidity.

INCORPORATION BY REFERENCE

All of the U.S. patents and U.S. published patent applications cited herein are hereby incorporated by reference. U.S. Pat. No. 5,512,490, issued Apr. 30, 1996, is hereby incorporated by reference in its entirety. U.S. patent application Ser. No. 11/040,504, filed Jan. 21, 2005, is hereby incorporated by reference in its entirety. U.S. patent application Ser. No. 10/398,157, filed Oct. 9, 2001, is hereby incorporated by reference in its entirety. U.S. patent application Ser. No. 09/287,573, filed Apr. 6, 1999, is hereby incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A coated microbead, comprising a microbead and a coating, wherein said coating comprises a fluorescent compound represented by I or a salt thereof:

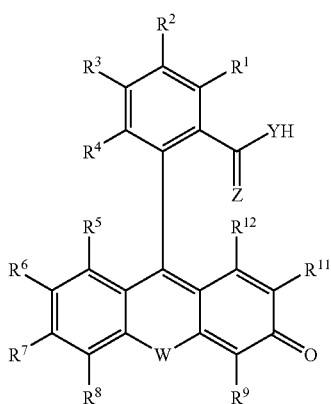

I wherein, independently for each occurrence, W is O, S, or $NR^4$; Y is O, S, or $NR^4$; Z is O or $NR^4$; $R^4$ is hydrogen, alkyl, acyl, or aralkyl; $R^1$, $R^2$, $R^3$, $R^4$, $R^5$, $R^6$, $R^7$, $R^8$, $R^9$, $R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and —$(CH_2)_m R^B$; $R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano; and m is 1-10 inclusive;

provided that at least one of $R^1$, $R^2$, $R^3$ and $R^4$ is

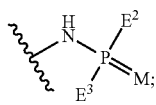

wherein M is O; $E^2$ is hydroxyl, alkoxy, aralkoxy, sulfhydryl, amino, trifluoroalkyl, —$O(CH_2)_n R^B$, —$NH(CH_2)_n R^B$, or —$S(CH_2)_n R^B$; $E^3$ is alkyl, cycloalkyl, heterocycloalkyl, aralkyl, heteroaralkyl, hydroxyl, alkoxy, aralkoxy, sulfhydryl, amino, or trifluoroalkyl; and n is 0-10 inclusive.

2. The coated microbead of claim 1, wherein Y is O; and Z is O.

3. The coated microbead of claim 1, wherein W is O.

4. The coated microbead of claim 1, wherein Y is O; Z is O; $R^1$ is H; $R^2$ is

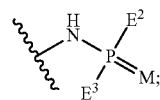

$R^3$ is H; and $R^4$ is H.

5. The coated microbead of claim 1, wherein Y is O; Z is O; and W is O.

6. The coated microbead of claim 1, wherein Y is O; Z is O; W is O; $R^5$ is H; $R^6$ is H; $R^7$ is OH; $R^8$ is H; $R^9$ is H; $R^{11}$ is H; and $R^{12}$ is H.

7. The coated microbead of claim 1, wherein $R^1$ is H; $R^2$ is

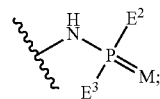

$R^3$ is H; $R^4$ is H; and W is O.

8. The coated microbead of claim 1, wherein $R^1$ is H; $R^2$ is

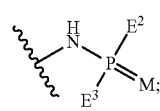

$R^3$ is H; $R^4$ is H; W is O; $R^5$ is H; $R^6$ is H; $R^7$ is OH; $R^8$ is H; $R^9$ is H; is H; and $R^{12}$ is H.

9. The coated microbead of claim 1, wherein Y is O; Z is O; $R^2$ is

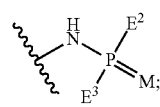

and $R^7$ is OH.

10. The coated microbead of claim 1, wherein Y is O; Z is O; $R^1$ is H; $R^2$ is

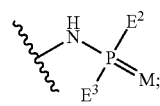

$R^3$ is H; $R^4$ is H; W is O; $R^5$ is H; $R^6$ is H; $R^7$ is OH; $R^8$ is H; $R^9$ is H; $R^{11}$ is H; and $R^{12}$ is H.

11. The coated microbead of claim 1, wherein said microbead comprises poly(2-vinylpyridine).

12. The coated microbead of claim 1, wherein said microbead comprises poly(2-vinylpyridine) and polystyrene.

13. The coated microbead of claim 1, wherein said microbead comprises poly(2-vinylpyridine) and a polystyrene functionalized with carboxylate moieties.

14. The coated microbead of claim 1, wherein said microbead comprises a polystyrene coated with poly(2-vinylpyridine), and said polystyrene is functionalized with carboxylate moieties.

15. The coated microbead of claim 1, wherein $E^2$ is alkoxy, amino, —O(CH$_2$)$_n$R$^B$, —NH(CH$_2$)$_n$R$^B$, or —S(CH$_2$)$_n$R$^B$.

16. The coated microbead of claim 1, wherein $E^2$ is ethoxy.

17. The coated microbead of claim 1, wherein $E^3$ is alkyl, cycloalkyl, or alkoxy.

18. The coated microbead of claim 1, wherein $E^3$ is methyl, ethyl, propyl, isopropyl, butyl, isobutyl, pentyl, isopentyl, 1,2,2-trimethylpropyl, cyclopentyl, cyclohexyl, or cycloheptyl.

19. The coated microbead of claim 1, wherein $E^3$ is methyl.

20. A method of detecting an analyte, comprising the steps of:
contacting an indicator with a sample comprising an analyte, thereby providing a fluorescent compound;
exposing the fluorescent compound to light at a first wavelength;
measuring the fluorescence of the fluorescent compound at a second wavelength; and
comparing the fluorescence of the fluorescent compound at the second wavelength to the fluorescence of the indicator at the second wavelength,
wherein
the analyte is a compound having structure C:

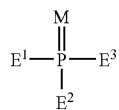

C wherein, independently for each occurrence,
M is O;
$E^1$ is F, Cl, Br, or I;
$E^2$ is hydroxyl, alkoxy, aralkoxy, sulfhydryl, amino, trifluoroalkyl, —O(CH$_2$)$_n$R$^B$, —NH(CH$_2$)$_n$R$^B$, or —S(CH$_2$)$_n$R$^B$;
$E^3$ is alkyl, cycloalkyl, heterocycloalkyl, aralkyl, heteroaralkyl, hydroxyl, alkoxy, aralkoxy, sulfhydryl, amino, or trifluoroalkyl;
n is 0-10 inclusive;
$R^B$ is hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, or cyano;
the fluorescent compound is represented by structure I or a salt thereof:

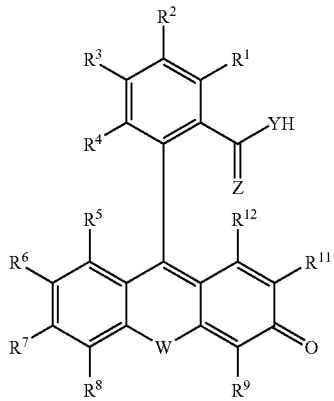

I wherein, independently for each occurrence,
W is O, S, or NR$^A$;
Y is O, S, or NR$^A$;
Z is O or NR$^A$;
$R^A$ is hydrogen, alkyl, acyl, or aralkyl;
$R^1$, $R^2$, $R^3$, $R^4$, $R^5$, $R^6$, $R^7$, $R^8$, $R^9$, $R^{11}$, and $R^{12}$ are independently selected from the group consisting of hydrogen, halide, pseudohalide, alkyl, aralkyl, alkenyl, alkynyl, cycloalkyl, heterocyclyl, aryl, heteroaryl, aralkyl, heteroaralkyl, carboxyl, acyl, carbamoyl, hydroxyl, alkoxy, aryloxy, aralkoxy, acyloxy, thio, sulfonyl, sulfhydryl, sulfamoyl, sulfonamido, sulfate, sulfonate, sulfoxido, seleno, nitro, amino, imino, amido, phosphonate, phosphinate, silyl, trifluoroalkyl, cyano, and —(CH$_2$)$_m$R$^B$; and
m is 1-10 inclusive;
provided that at least one of $R^1$, $R^2$, $R^3$ and $R^4$ is

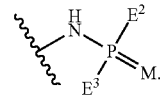

* * * * *